(12) United States Patent
Yoon et al.

(10) Patent No.: US 10,337,044 B2
(45) Date of Patent: Jul. 2, 2019

(54) **KANAMYCIN COMPOUND, KANAMYCIN-PRODUCING *STREPTOMYCES* SPECIES BACTERIUM, AND METHOD OF PRODUCING KANAMYCIN**

(71) Applicant: iNtRON Biotechnology, Inc., Seongnam-si (KR)

(72) Inventors: Yeo Joon Yoon, Seoul (KR); Sung Ryeol Park, Goyang-si (KR); Je Won Park, Goyang-si (KR); Jae Kyung Sohng, Asan-si (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 423 days.

(21) Appl. No.: 14/831,519

(22) Filed: Aug. 20, 2015

(65) Prior Publication Data

US 2016/0040206 A1  Feb. 11, 2016

Related U.S. Application Data

(62) Division of application No. 13/642,842, filed as application No. PCT/KR2010/007041 on Oct. 14, 2010, now Pat. No. 9,133,492.

(30) Foreign Application Priority Data

Apr. 23, 2010 (KR) .................. 10-2010-0037709
Aug. 25, 2010 (KR) .................. 10-2010-0082418

(51) Int. Cl.
| | | |
|---|---|---|
| *C12N 15/52* | (2006.01) | |
| *C12N 15/74* | (2006.01) | |
| *C12N 1/20* | (2006.01) | |
| *C12P 19/48* | (2006.01) | |
| *A61K 31/351* | (2006.01) | |
| *A61K 31/7036* | (2006.01) | |
| *C07H 15/22* | (2006.01) | |
| *C07H 15/234* | (2006.01) | |
| *C12N 15/76* | (2006.01) | |
| *C12R 1/61* | (2006.01) | |

(52) U.S. Cl.
CPC .......... *C12P 19/485* (2013.01); *A61K 31/351* (2013.01); *A61K 31/7036* (2013.01); *C07H 15/22* (2013.01); *C07H 15/234* (2013.01); *C12N 15/52* (2013.01); *C12N 15/76* (2013.01); *C12R 1/61* (2013.01); *Y02A 50/473* (2018.01)

(58) Field of Classification Search
None
See application file for complete search history.

(56) References Cited

U.S. PATENT DOCUMENTS 4,208,531 A * 6/1980 Canas-Rodriquez ........................ C07H 15/234
536/13.6
5,200,327 A    4/1993 Garvin et al.

FOREIGN PATENT DOCUMENTS

| KR | 1991-0003096 A | 2/1991 |
| KR | 2003-0013450 A | 2/2003 |
| WO | 2007/041156 A2 | 4/2007 |

OTHER PUBLICATIONS

Search of 11725BP at Korean Collection for Type Cultures. Conducted on Jun. 12, 2017. 1 page.*
Search of 11726BP at Korean Collection for Type Cultures. Conducted on Jun. 12, 2017. 1 page.*
Search of 11727BP at Korean Collection for Type Cultures. Conducted on Jun. 12, 2017. 1 page.*
Search of 11728BP at Korean Collection for Type Cultures. Conducted on Jun. 12, 2017. 1 page.*
Kharel et al. A gene cluster for biosynthesis of kanamycin from *Streptomyces kanamyceticus*: Comparison with gentamicin biosynthetic gene cluster. Jul. 20, 2004. Arch. Biochem Biophys. vol. 429, p. 204-214.*
Li et al. Biosynthesis of the Unique Amino Acid Side Chain of Butirosin: Possible Protective-Group Chemistry in an Acyl Carrier Protein-Mediated Pathway. Jun. 2005. Chemistry & Biology. vol. 12, pp. 665-675.*
Park et al. Genetic dissection of the biosynthetic route to gentamicin A2 by heterologous expression of its minimal gene set. Jun. 12, 2008. Proceedings National Academy of Sciences USA. vol. 105, No. 24, pp. 8399-8404.*

(Continued)

*Primary Examiner* — Channing S Mahatan
(74) *Attorney, Agent, or Firm* — Seed IP Law Group LLP

(57) ABSTRACT

Vectors expressing kanA-kanB-kanK and other kanamycin production-related genes, *Streptomyces* species recombinant bacteria transformed with the vectors, a method of producing kanamycin antibiotics by the bacteria, and a new kanamycin compound produced by the bacterium are provided. With the use of the recombinant bacteria of the present invention, the direct fermentative biosynthesis of amikacin and tobramycin as semi-synthetic kanamycins is possible, and the yield of kanamycin B as a precursor of the semi-synthetic kanamycin is improved.

11 Claims, 12 Drawing Sheets
Specification includes a Sequence Listing.

(56) References Cited

OTHER PUBLICATIONS

Kudo et al. Enzymatic activity of a glycosyltransferase KanM2 encoded in the kanamycin biosynthetic gene cluster. 2009. The Journal of Antibiotics. vol. 62, pp. 707-710.*

Llewellyn et al. Biosynthesis of Butirosin: Transfer and Deprotection of the Unique Amino Acid Side Chain. Apr. 2007. Chemistry & Biology. vol. 14, pp. 379-386.*

Llewellyn et al. Chennoenzynnatic acylation of aminoglycoside antibiotics. Jun. 20, 2008. Chem. Commun. pp. 3786-3788. (Year: 2008).*

Nepal et al., "Heterologous Production of Paromamine in *Streptomyces lividans* TK24 Using Kanamycin Biosynthetic Genes from *Streptomyces kanamyceticus* ATCC12853," *Mol. Cells* 27:601-608, May 31, 2009.

Park, "Characterization of the Biosynthetic Route to 4, 6-disubstituted Aminoglycosides using Heterologous Expression System," Ph.D. Dissertation, Ewha University, February.

* cited by examiner

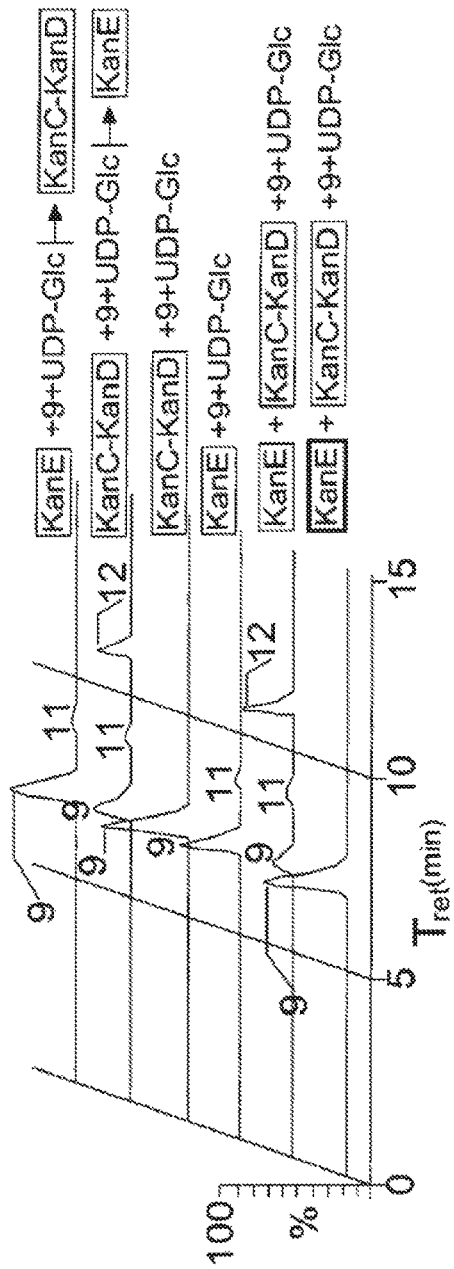
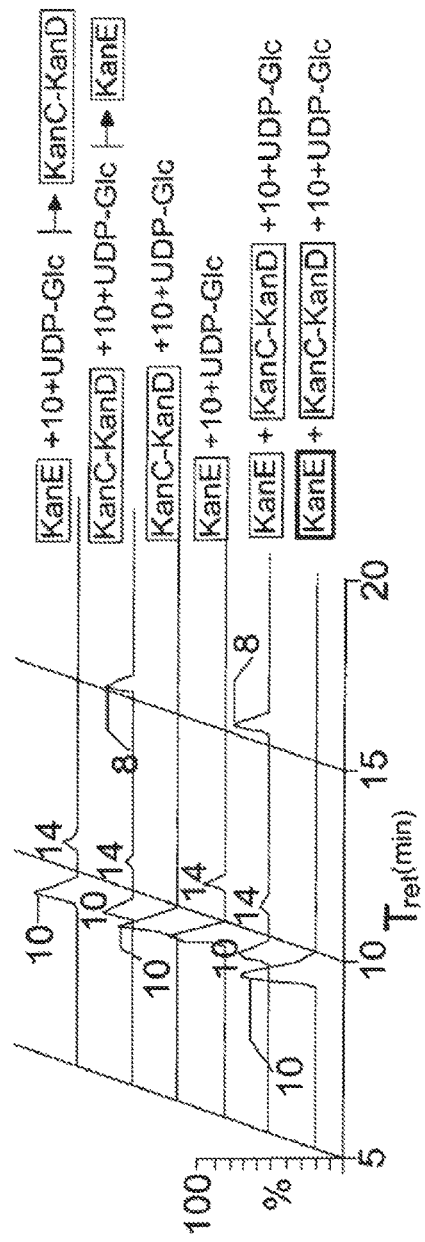
Fig. 6A
Fig. 6B

[Fig. 7]
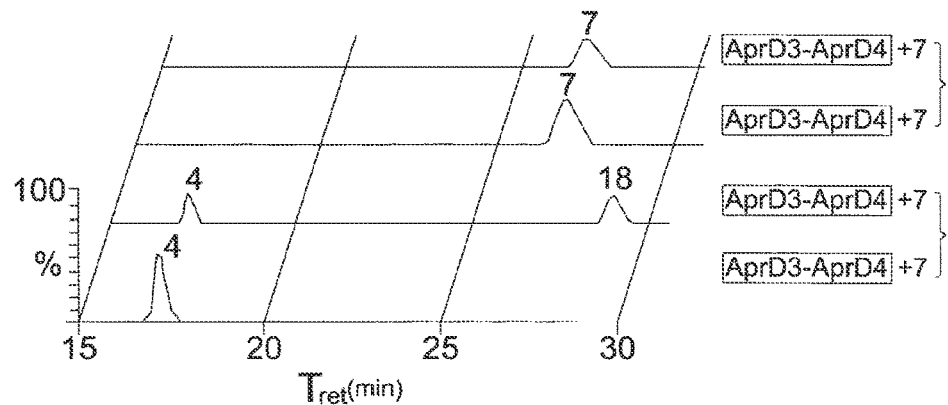
[Fig. 8]
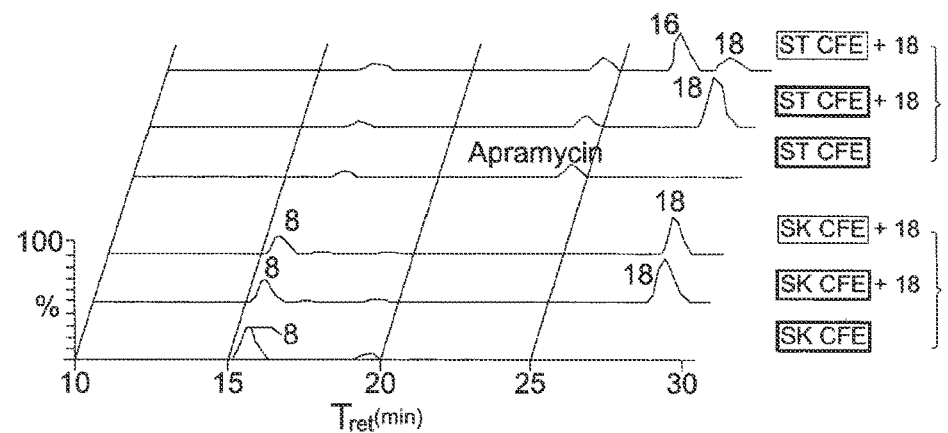
[Fig. 9]
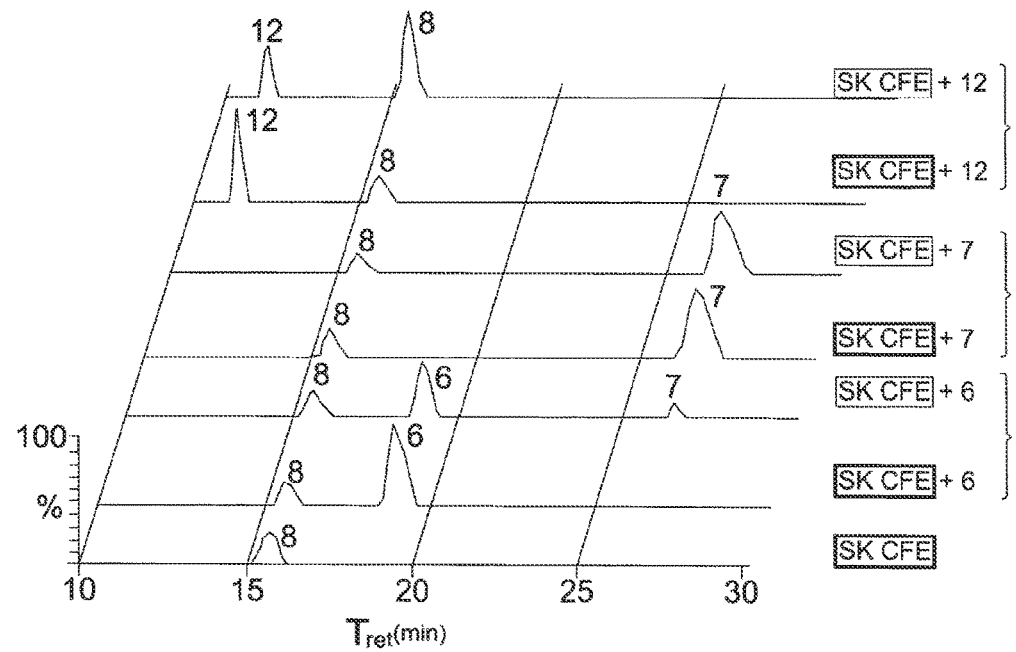

KANAMYCIN COMPOUND, KANAMYCIN-PRODUCING *STREPTOMYCES* SPECIES BACTERIUM, AND METHOD OF PRODUCING KANAMYCIN

TECHNICAL FIELD

The present invention relates to a new kanamycin compound, a kanamycin-producing *Streptomyces* species bacterium, and a method of producing kanamycin using the bacterium.

BACKGROUND ART

Kanamycin produced by *Streptomyces kanamyceticus* is a 4,6-disubstituted 2-deoxystreptamine-containing aminoglycoside antibiotic as are gentamicins and tobramycin, whereas neomycins and butirosins are 4,5-disubstituted aminoglycosides.

These types of antibiotics are produced mainly by actinomycetes and have been widely used for a long time. Like other antibiotics, the appearance of aminoglycoside-resistant bacteria, which produce aminoglycoside-modifying enzymes, cause serious problems. The issue of resistance has been addressed by the semi-synthetic variants of naturally-occurring aminoglycosides such as amikacin, dibekacin, and arbekacin. The central 2-deoxystreptamine (2-DOS) and pseudodisaccharides 2'-N-acetylparomamine, paromamine, and neamine are common biosynthetic intermediates of most aminoglycosides. The biosynthetic route to neamine via 2-deoxystreptamine and paromamine was elucidated using recombinant enzymes involved in butiroin and neomycin biosynthesis.

DISCLOSURE OF INVENTION

Technical Problem

It has been reported a glycosyltransferase (GT) KanE (also called KanM2) from the kanamycin cluster, catalyzes the glycosylation of paromamine to produce 3''-deamino-3''-hydroxykanamycin C using uridine 5'-diphospho-D-glucose (UDP-Glc) as a cosubstrate. Alternatively, it is considered that kanamycin C and kanamycin B are produced as kanosamine (Kns: D-3-glucosamine) is transferred to paromamine and neamine, respectively, by KanE. Otherwise, it is considered that 3''-deamino-3''-hydroxykanamycin C is a precursor of kanamycin C, which can produce kanamycin B as position C-6' of kanamycin C is aminated. It is also considered that kanamycin A can be synthesized by either KanE-catalyzed addition of kanosamine to 2'-deamino-2'-hydroxyneamine or by deamination of the posetion C-2' of kanamycin B. However, the biosynthesis of kanamycin from pseudodisaccharides or 3''-deamino-3''-hydroxykanamycin C has not been well known. The reason for this is that it is difficult to engineer aminoglycoside-producing actinomycetes genetically and obtain functional, soluble biosynthetic enzymes.

The inventors of the present invention have constructed an effective heterologous expression system based on an engineered strain of *S. venezuelae* and elucidated the biosynthesis of gentamicin $A_2$.

Therefore, an object of the present invention is to elucidate the biosynthetic pathway of kanamycins and provide a method of producing kanamycin compounds and a new antibiotic produced by the same.

Solution to Problem

Recently, the inventors of the present invention isolated the kanamycin biosynthetic gene cluster from *S. kanamyceticus*. The production of kanamycin A by expression of this entire cluster in an aminoglycoside non-producing *S. venezuelae* indicated it contains all of the genes sufficient for the biosynthesis of the kanamycin comlpex.

Therefore, the object of the present invention can be achieved by a vector comprising kanA-kanB-kanK and other kanamycin biosynthetic genes, a *Streptomyces* species bacterium transformed with the vector, a method for production of kanamycin by the bacterium, and a new kanamycin compound produced by the bacterium.

Advantageous Effects of Invention

According to the present invention, a kanamycin-producing *Streptomyces* species bacterium, a method for effective production of kanamycin, and a new kanamycin compound produced by the same are provided.

BRIEF DESCRIPTION OF DRAWINGS

The above and other features and advantages of the present invention will be more clearly understood from the following detailed description taken in conjunction with the accompanying drawing, in which:

In FIG. 1A, kanamycin, tobramycin, and gentamicin are 4,6-disubstituted aminoglycosides, whereas butirosins and neomycins are 4,5-disubstituted aminoglycosides. They are all naturally-occurring products, whereas amikacin, dibekacin, and arbekacin are semi-synthetic aminoglycosides derived from kanamycins. AHBA is S-4-amino-2-hydroxybutyric acid. FIG. 1B shows the biosynthesis of compound 5 (solid lines). However, a complete biosynthetic pathway (dotted lines) for compound 8 as a final product has not been discovered. 2-DOI: 2-deoxy-scyllo-inosose; 2-DOIA: 2-deoxy-scyllo-inosamine; UDP-GlcNAc: uridine 5'-diphospho-D-2-N-acetylglucosamine; and UDP-Glc: UDP-D-glucose.

FIG. 2A shows the chromatograms of extracts from the recombinants (2-DOS, DOSf, and PAR) expressing kanA-kanB-kanK (2-DOS biosynthetic genes), kanA-kanB-kanK-kanF (kanF is a gene encoding the first glycosyltransferase), and kanA-kanB-kanK-kanF-kacA (kacA is a gene encoding deacetylase). Each colored block represents an annotated gene. FIG. 2B shows the chromatograms of compounds 2 and 9 produced by the first glycosyltransferase KanF using three kinds of UDP sugars such as UDP-glucose (Glc), UDP-2-N-acetylglucosamine (GlcNAc), and UDP-2-glucosamine (GlcN) as substrates. Each box represents the cell-free extract obtained from the recombinant host expressing kanF, and black-framed boxes indicate the boiled cell-free extracts as controls. FIG. 2C shows the chromatograms of extracts from the recombinant (PARcd) expressing kanA-kanB-kanK-kanF-kacA and kanC-kanD at the same time and the recombinant (PARil) expressing kanA-kanB-kanK-kanF-kacA and kanI-kacL at the same time. FIG. 2D shows the chromatograms of compounds 4 and 10 produced by KanI-KacL-catalyzed reaction using paromamine and 2'-deamino-2'-hydroxyparomamine as substrates. FIG. 2E shows the chromatograms of the extracts from the recombinant (KCXΔcΔd) expressing kanA-kanB-kanK-kanF-kacA-kanE, the recombinant (KCX) expressing kanA-kanB-kanK-kanF-kacA-kanE-kanC-kanD, the recombinant (KABΔcΔd) expressing kanA-kanB-kanK-kanF-kacA-kanE-kanI-kacL, and the recombinant (KAB) expressing kanA-kanB-kanK-kanF-kacA-kanE-kanC-kanD-kanI-kacL. FIG. 2F shows the chromatograms of KanC-KanD and KanE-catalyzed production of compounds 5 and 6, supplemented with paromamine and UDP-Glc. Arrows represent quenching of sequential reactions. FIG. 2G shows the chromatograms of KanC-KanD and KanE-catalyzed production of compounds 7 and 13, supplemented with paromamine and UDP-Glc. FIG. 2H shows the chromatograms of the KanI-KacL-catalyzed production of compounds 7 and 8.

FIG. 4A shows the chromatograms of extracts from the recombinants expressing kanA-kanB-kanK and kanF (DOSf), nemD (DOSn), tobM1 (DOSt$_1$) or gtmG (DOSg) at the same time, in which the bar graph on the right side shows the yield of kanamycin pseudodisaccharide intermediates produced by each recombinant strain. The white bar indicates compound 2 and the gray bar indicates compound 9. Data were obtained from triplicate analyses. FIG. 4B shows the chromatograms of extracts from recombinants (KCX, KCXΔfn, KCXΔft$_1$, and KCXΔfg) expressing one of kanA-kanB-kanK-kacA-kanE-kanC-kanD, together with kanF, nemD, tobM1, or gtmG. The bar graph shows the yield of kanamycin pseudodisaccharides produced by each recombinant strain. The white bar indicates compounds 5 and 6, which are the congeners of compound 7 in the left-hand cycle of the decalcomania-like biosynthetic pathway. The gray bars indicate yields of compounds 11 and 12, which are the congeners of compound 8 in the right-hand cycle. FIG. 4C shows the chromatograms of extracts from recombinants (KAB and KABΔfn) expressing one of kanA-kanB-kanK-kacA-kanE-kanC-kanD-kanI-kacL together with kanE or nemD, in which the bar graph shows the yield of kanamycin produced by each recombinant. The white bars indicate the production of compounds 6 and 7, and the gray bar represents the production of compounds 12 and 8.

FIG. 5A shows the chromatograms of the products from the recombinant (KCXb) expressing a compound 12-producing gene set (kanA-kanB-kanK-kacA-kanE-kanC-kanD) together with seven butirosin biosynthetic genes (btrG-btrH-btrI-btrJ-btrK-btrO-btrV) or the recombinant (KABb) expressing a compound 8-producing gene set (kanA-kanB-kanK-kacA-kanE-kanC-kanD-kanI-kacL). Compound 15 is the AHBA-conjugated kanamycin derivative amikacin and compound 17 is the previously uncharacterized AHBA-conjugated kanamycin derivative 1-N-AHBA-kanamycin X. FIG. 5B shows the chromatograms of the products from the recombinants (KABΔfna and KABΔSnΔet$_2$a) expressing aprD3-aprD4 and a compound 8-biosynthetic gene set such as kanA-kanB-kanK-nemD-kacA-kanE-kanC-kanD-kanI-kacL or kanA-kanB-kanK-nemD-kacA-tobM2-kanC-kanD-kanI-kacL at the same time. Compounds 16 and 18 are tobramycin and nebramine as a tobramycin biosynthetic intermediate. FIG. 5C shows the structures of kanamycin analogs produced by the recombinants expressing aprD3-aprD4 and tobM2 genes. Each colored-circle represents the functional group formed by the product of the gene with annotation information shown by the same colored block.

FIGS. 6A and 6B show the results of HPLC-ESI-MS/MS analysis of kanamycin pseudodisaccharides obtained from in vitro reactions using cell-free extracts of recombinant *S. venezuelae* strains expressing kanE and kanC-kanD, respectively. FIG. 6A shows the chromatograms of the production of compounds 11 and 12. Each box represents the cell-free extract obtained from the recombinant host expressing kanE or kanC-kanD, black-framed boxes indicate the boiled cell-free extracts as controls, and arrows represent quenching of sequential reactions. FIG. 6B shows the chromatograms of the production of compounds 8 and 14.

FIG. 7 shows the results of HPLC-ESI-MS/MS analysis of compounds 16 and 18 produced from in vitro reactions using cell-free extracts of recombinant *S. venezuelae* strains expressing aprD3-aprD4 gene pair. Each box represents the cell-free extract obtained from the recombinant host expressing aprD3-aprD4 gene pair, and black-framed boxes indicate boiled cell-free extracts as controls.

FIG. 8 shows the results of HPLC-ESI-MS/MS analysis of compounds 16 produced from in vitro reactions using cell-free extracts of wild strains of *S. kanamyceticus* and *Streptomyces* tenebrarius. Each box represents the cell-free extract obtained from *S. kanamyceticus* ATCC 12853 (SK CFE) and *S. tenebrarius* ATCC 17920 (ST CFE), and black-framed boxes indicate boiled cell-free extracts as controls.

FIG. 9 shows the results of HPLC-ESI-MS/MS analysis of kanamycin pseudodisaccharides obtained from in vitro reactions using cell-free extracts of wild-type *S. kanamyceticus* strain. Each box represents the cell-free extract obtained from the *S. kanamyceticus* ATCC 12853 (SK CFE), and black-framed boxes indicate boiled cell-free extracts as controls.

BEST MODE FOR CARRYING OUT THE INVENTION

Figure 1A:
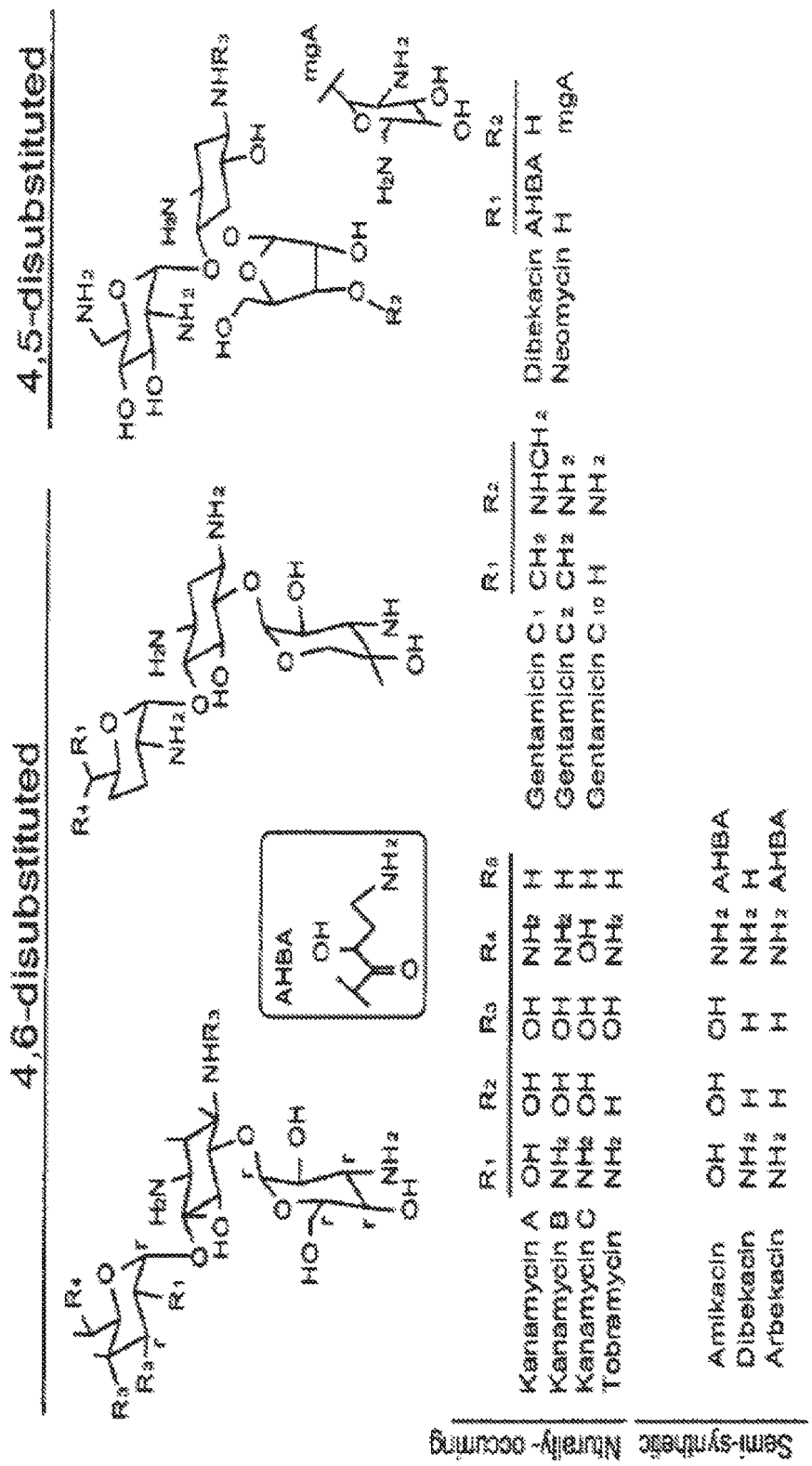
FIG. 1A shows the structures of 2-DOS-containing aminoglycosides and FIG. 1B shows the previously proposed biosynthetic pathway of kanamycins.

The present invention provides a vector comprising at least one gene set selected from the group consisting of:

(1) kanA, kanB, and kanK (DOS strain);
(2) kanA, kanB, kanK, and kanF (DOSf strain);
(3) kanA, kanB, kanK, kanF, and kacA (PAR strain);
(4) kanA, kanB, kanK, kanF, kacA, kanC, and kanD (PARcd strain);
(5) kanA, kanB, kanK, kanF, kacA, kanI, and kacL (PARi1 strain);
(6) kanA, kanB, kanK, kanF, kacA, and kanE (KCXΔcΔd strain);
(7) kanA, kanB, kanK, kanF, kacA, kanE, kanC, and kanD (KCX strain);
(8) kanA, kanB, kanK, kanF, kacA, kanE, kanI, and kacL (KABΔcΔd strain);
(9) kanA, kanB, kanK, kanF, kacA, kanE, kanC, kanD, kanI, and kacL (KAB strain);
(10) kanA, kanB, kanK, kanF, kacA, kanE, kanC, kanD, btrG, btrH, btrI, btrJ, btrK, btrO, and btrV (KCXb strain);

(11) kanA, kanB, kanK, kanF, kacA, kanE, kanC, kanD, kanI, kacL, btrG, btrH, btrI, btrJ, btrK, btrO, and btrV (KABb strain);
(12) kanA, kanB, kanK, and nemD (DOSn strain);
(13) kanA, kanB, kanK, nemD, kacA, kanE, kanC, and kanD (KCXΔfn strain);
(14) kanA, kanB, kanK, nemD, kacA, kanE, kanC, kanD, kanI, and kacL (KABΔfn strain);
(15) kanA, kanB, kanK, nemD, kacA, kanE, kanC, kanD, kanI, kacL, aprD3, and aprD4 (KABΔfna strain);
(16) kanA, kanB, kanK, nemD, kacA, tobM2, kanC, kanD, kanI, kacL, aprD3, and aprD4 (KABΔfnΔet₂a strain);
(17) kanA, kanB, kanK, and tobM1 (DOSt₁ strain);
(18) kanA, kanB, kanK, tobM1, kacA, kanE, kanC, and kanD (KCXΔft₁ strain);
(19) kanA, kanB, kanK, and gtmG (DOSg strain); and
(20) kanA, kanB, kanK, gtmG, kacA, kanE, kanC, and kanD (KCXΔfg strain), and
a kanamycin-producing recombinant *Streptomyces* species bacterium transformed with the vector.

Preferably, the kanA, kanB, kanK, kanF, kacA, kanE, kanC, kanD, kanI, and kacL are derived from *Streptomyces kanamyceticus* and have sequence numbers 5 to 14.

The aprD3, aprD4, tobM1, and tobM2 are derived from *Streptomyces tenebrarius* and have sequence numbers 15 to 18.

The btrG, btrH, btrI, btrJ, btrK, btrO, and btrV are derived from *Bacillus circulans* and have sequence numbers 19 to 25.

The nemD is derived from *Streptomyces fradiae* and has sequence number 26.

The gtmG is derived from *Micromonospora echinospora* and has sequence number 4.

Preferably, the *Streptomyces* species bacterium further expresses a kanamycin-resistant gene. Preferably, the kanamycin-resistant gene comprises gtmF, gtmK, and gtmL derived from *Micromonospora echinospora*, which have sequence numbers 1 to 3.

The *Streptomyces* species bacterium is *Streptomyces venezuelae*, but not limited thereto. Preferably, the *Streptomyces* species bacterium is *Streptomyces venezuelae* KCTC11725BP and, more preferably, the *Streptomyces* species bacterium is *Streptomyces venezuelae* KCTC11726BP. The *Streptomyces* species bacterium is *Streptomyces venezuelae* KCTC11727BP and, preferably, the *Streptomyces* species bacterium is *Streptomyces venezuelae* KCTC11728BP.

Moreover, the present invention provides a method of producing a kanamycin antibiotic using the *Streptomyces* species bacterium, and the kanamycin antibiotic produced by the present invention comprises the following compounds 1 to 20:
Compound 1: 2-deoxystreptamine (2-DOS)
Compound 2: 2'-N-acetylparomamine;
Compound 3: paromamine;
Compound 4: neamine;
Compound 5: 3"-deamino-3"-hydroxykanamycin C;
Compound 6: kanamycin C;
Compound 7: kanamycin B;
Compound 8: kanamycin A;
Compound 9: 2'-deamino-2'-hydroxyparomamine;
Compound 10: 2'-deamino-2'-hydroxyneamine;
Compound 11: 3"-deamino-3"-hydroxykanamycin X;
Compound 12: kanamycin X;
Compound 13: 3"-deamino-3"-hydroxykanamycin B;
Compound 14: kanamycin D;
Compound 15: amikacin;
Compound 16: tobramycin;
Compound 17: 1-N-AHBA-kanamycin X;
Compound 18: nebramine;
Compound 19: 3'-deoxykanamycin C; and
Compound 20: 3'-deoxykanamycin A.

Moreover, the products obtained from the recombinant bacteria are as follows:
DOS: compound 1;
DOSf: compounds 2 and 9;
PAR: compounds 3 and 9;
PARcd: compounds 3 and 9;
PARi1: compounds 4 and 10;
KCXΔcΔd: compounds 5 and 11;
KCX: compounds 6 and 12;
KABΔcΔd: compounds 13 and 14;
KAB: compounds 7 and 8;
KCXb: compound 17;
KABb: compound 15;
DOSn: compounds 2 and 9;
KCXΔfn: compounds 6 and 12;
KABΔfn: compounds 7 and 8;
KABΔfna: compounds 18, 19 and 20;
KABΔfnΔet₂a: compound 16;
DOSt₁: compounds 2 and 9;
KCXΔft₁: compounds 6 and 12;
DOSg: compounds 2 and 9; and
KCXΔfg: compounds 6 and 12.

When the kanamycin is produced by the gene recombinant bacteria of the present invention, especially KABΔfn strain, the yield of kanamycin B as a precursor of arbekacin, which is one of the semi-synthetic aminoglycosides, is improved compared to wild-type strains.

Moreover, with the use of the gene recombinant bacteria of the present invention, especially KABb and KABΔfnΔet₂a strains, it is possible to produce amikacin and tobramycin by direct fermentation, not by semi-fermentation and semi-synthesis.

Furthermore, the present invention provides a new compound represented by the following formula 1:

[Formular 1]

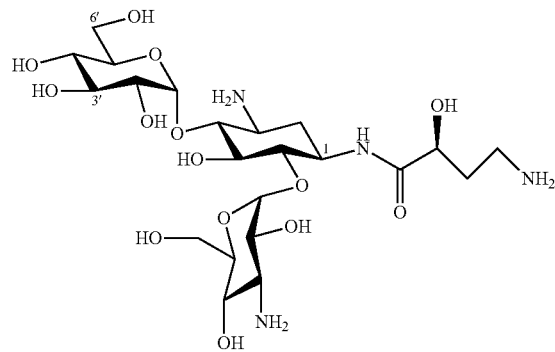

The new compound is compound 17, 1-N-AHBA-kanamycin X.

The kanamycin compound of the present invention produced by the bacterium of the present invention has an antibacterial effect. More particularly, the compound of the present invention has an antibacterial effect on Gram-negative bacteria. The compound has an antibacterial effect on *Pseudomonas aeruginosa* and *Escherichia coli*, but not limited thereto. Especially, the new compound, 1-N-AHBA-kanamycin X, has an antibacterial effect on amikacin-resistant *P. aeruginosa*.

Recently, various studies have reported that aminoglycoside antibiotics containing the 2-DOS have antiviral effects on various viruses such as bovine viral diarrhea virus (BVDV), dengue virus (DENV), etc. Moreover, many studies have reported that the aminoglycoside antibiotics, which induce mammalian ribosomes to readthrough premature stop codon mutations, can treat and improve hereditary diseases such as cystic fibrosis, muscular atrophy, Hurler syndrome, telangiectasis, and Usher syndrome. The kanamycin compound of the present invention also contains the 2-DOS as a fundamental structure, and thus it is considered that the kanamycin compound of the present invention has an antiviral effect and can treat and improve such hereditary diseases.

Therefore, the present invention provides an antibacterial composition comprising the kanamycin compound as an effective ingredient.

Moreover, the present invention provides an antiviral composition comprising the kanamycin compound as an effective ingredient.

Furthermore, the present invention provides a pharmaceutical composition comprising the kanamycin compound as an effective ingredient for the treatment of at least one disease selected from the group consisting of cystic fibrosis, muscular atrophy, Hurler syndrome, telangiectasis, and Usher syndrome.

The composition may be administered orally, rectally, vaginally, topically, transdermally, intravenously, intramuscularly, intraperitoneally, or subcutaneously. The effective dose of the active compound may vary depending on the minimum inhibitory concentration (MIC), the age and condition of the patient, particular disease, the severity of disease or condition, the route of administration, and administrator s decision.

The pharmaceutical composition may be medicated in the form of solid, semi-solid, or liquid depending on an administration pattern. It may include tablets, powders, suppositories, granules, creams, lotions, ointments, patches, aqueous solutions, suspensions, dispersions, emulsions, syrups, but are not limited to them. Active ingredients can be encapsulated in liposomes, nanoparticles, microcapsules, etc. Solid compositions such as tablets, pills, granules, etc. may be coated for convenience.

The composition of the present invention may contain pharmaceutically acceptable excipients such as diluents, carriers, isotoners, stabilizers, antioxidants, binders, colorants, flavorings, preservatives, thickening agents, etc. Such excipients can be selected by one skilled in the art according to the administration routes and formulations. Moreover, the composition of the present invention may contain a small amount of a non-toxic adjuvant such as a wetting agent, emulsifier, pH buffer agent, etc. The non-toxic adjuvant may include, but not limited to, acetate, sorbitan monolaurate, triethanolamine, and triethanolamine oleate. The composition for intravenous administration may be a solution in sterile isotonic aqueous buffer solution and may contain a local anesthetic for relief of pain in the injection area.

TABLE 1

Deoxyoligonucleotide primers used for PCR amplification of genes

| Gene | Primer sequence(5' to 3', restriction site shown with underline) | Portion of gene | Enzyme site |
|---|---|---|---|
| kanA-kanB | cccggatccgaatcccccttcgtgacg (SEQ ID NO: 27) | 5' | BamHI |
|  | gtgactagtgttcgtcgaccaccgcgtcga (SEQ ID NO: 28) | 3' | SpeI |
| kanK | gcttctagaactccggagcacccgtgca (SEQ ID NO: 29) | 5' | XbaI |
|  | gtgaagcttcgtggtgccggacaggccta (SEQ ID NO: 30) | 3' | HindIII |
| kanC | gggacctctagaacgcggtggtcgacgaac (SEQ ID NO: 31) | 5' | XbaI |
|  | tcttccaagcttactagttgtcggcggtcgccccga (SEQ ID NO: 32) | 3' | SpeI/HindIII |
| kanD | gaccgctctagacacctccgaggtcctctc (SEQ ID NO: 33) | 5' | XbaI |
|  | tgaaaagcttactagtgggtgacgagacgccggg (SEQ ID NO: 34) | 3' | SpeI/HindIII |
| kanE | acatctagaggctccggaagaccgccgacgcca (SEQ ID NO: 35) | 5' | XbaI |
|  | tcgaagcttactagtgagacgaggaggaccctt (SEQ ID NO: 36) | 3' | SpeI/HindIII |
| kanF | cgaggctctagagccggaccagaacccatt (SEQ ID NO: 37) | 5' | XbaI |
|  | tagaacaagcttactagtacgtcgggtgtcgtacgg (SEQ ID NO: 38) | 3' | SpeI/HindIII |
| kanI-kacL | gatcgctctagacacctggttctggttccc (SEQ ID NO: 39) | 5' | XbaI |
|  | aggggaaagcttactagtgtcaggagatgccgaccg (SEQ ID NO: 40) | 3' | SpeI/HindIII |

TABLE 1-continued

Deoxyoligonucleotide primers used for PCR amplification of genes

| Gene | Primer sequence (5' to 3', restriction site shown with underline) | Portion of gene | Enzyme site |
| --- | --- | --- | --- |
| kacA | ggcgtctagataccgggagatcgggctgtg (SEQ ID NO: 41) | 5' | XbaI |
| | acaaagcttactagttgctcatagcgactccttgt (SEQ ID NO: 42) | 3' | SpeI/HindIII |
| nemD | cactctagacatcgccgtcctctcccgt (SEQ ID NO: 43) | 5' | XbaI |
| | tcaaagcttactagtggcgcagatacggcgcac (SEQ ID NO: 44) | 3' | SpeI/HindIII |
| tobM1 | ccgtctagaccgcccttccccgcaac (SEQ ID NO: 45) | 5' | XbaI |
| | gataagcttactagtcacaccgtcctattcctg (SEQ ID NO: 46) | 3' | SpeI/HindIII |
| tobM2 | cgatctagaccgggaggcgaccgtgt (SEQ ID NO: 47) | 5' | XbaI |
| | gcgaagcttactagttcagacgcatacgcccag (SEQ ID NO: 48) | 3' | SpeI/HindIII |
| gtmG | tgtcctctagagctgcccggtcacttcccgc (SEQ ID NO: 49) | 5' | XbaI |
| | aaaaagcttactagtcactcttccggaagaatc (SEQ ID NO: 50) | 3' | SpeI/HindIII |
| btrG-btrH | ttctctagatctaggaaaccgcatgcc (SEQ ID NO: 51) | 5' | XbaI |
| | ggctacgtaaaactagtggtttatccgcttttgct (SEQ ID NO: 52) | 3' | SpeI/SnaBI |
| btrI-btrJ | acctctagacggaaaccgccatcccat (SEQ ID NO: 53) | 5' | XbaI |
| | tcctacgtaaaactagtgagttaatgaacagccgt (SEQ ID NO: 54) | 3' | SpeI/SnaBI |
| btrK-btrO | agctctagaaagcccgaagcctgcttg (SEQ ID NO: 55) | 5' | XbaI |
| | gtttacgtaaaactagttccctagaccggattcga (SEQ ID NO: 56) | 3' | SpeI/SnaBI |
| btrV | tattctagaattgacttataactcaat (SEQ ID NO: 57) | 5' | XbaI |
| | cattacgtaaaactagtatccgaacgtcacataag (SEQ ID NO: 58) | 3' | SpeI/SnaBI |
| aprD3 | ggttctagatgatggacgtggccgcga (SEQ ID NO: 59) | 5' | XbaI |
| | cttaagcttactagtgggccgtcggtcgtcctg (SEQ ID NO: 60) | 3' | SpeI/HindIII |
| aprD4 | ggctctagaaaccccaccctcaccatccag (SEQ ID NO: 61) | 5' | XbaI |
| | cgcaagcttactagtatcgtgtggtctccggct (SEQ ID NO: 62) | 3' | SpeI/HindIII |

The inventors of the present invention have reconstructed a complete biosynthesis of kanamycin by integrating the plasmid containing various candidate genes isolated from *S. kanamyceticus* into *S. venezuelae* strain, which is deficient in biosynthesis of the endogenous deoxysugar thymidine 5'-diphospho (TDP)-D-desosamine. The inventors have amplified putative kanamycin biosynthetic genes by PCR with specific primers shown in table 1.

The inventors have modified the kanamycin biosynthetic flux to produce kanamycin B (compound 7) as a main product. The reason for this is that the production of compound 7 leads to the production of 3'-deoxykanamycin and 1-N-AHBA kanamycin by direct fermentation, which will be valuable substitutes for the chemical synthesis of dibekacin and arbekacin.

After examining the kanamycin analogs obtained from the recombinants and their structures, it has been confirmed that the kanamycin antibiotic, which is known as one of the compounds produced from the recombinant bacteria of the present invention, has the same properties as the commercially available standard kanamycin analog or the kanamycin analog derived from *S. kanamyceticus*. However, it has been ascertained that 1-N-AHBA-kanamycin X, a new kanamycin analog, has been produced by the recombinant heterologous strain of the present invention in addition to the conventional kanamycin antibiotics.

Figure 1B:
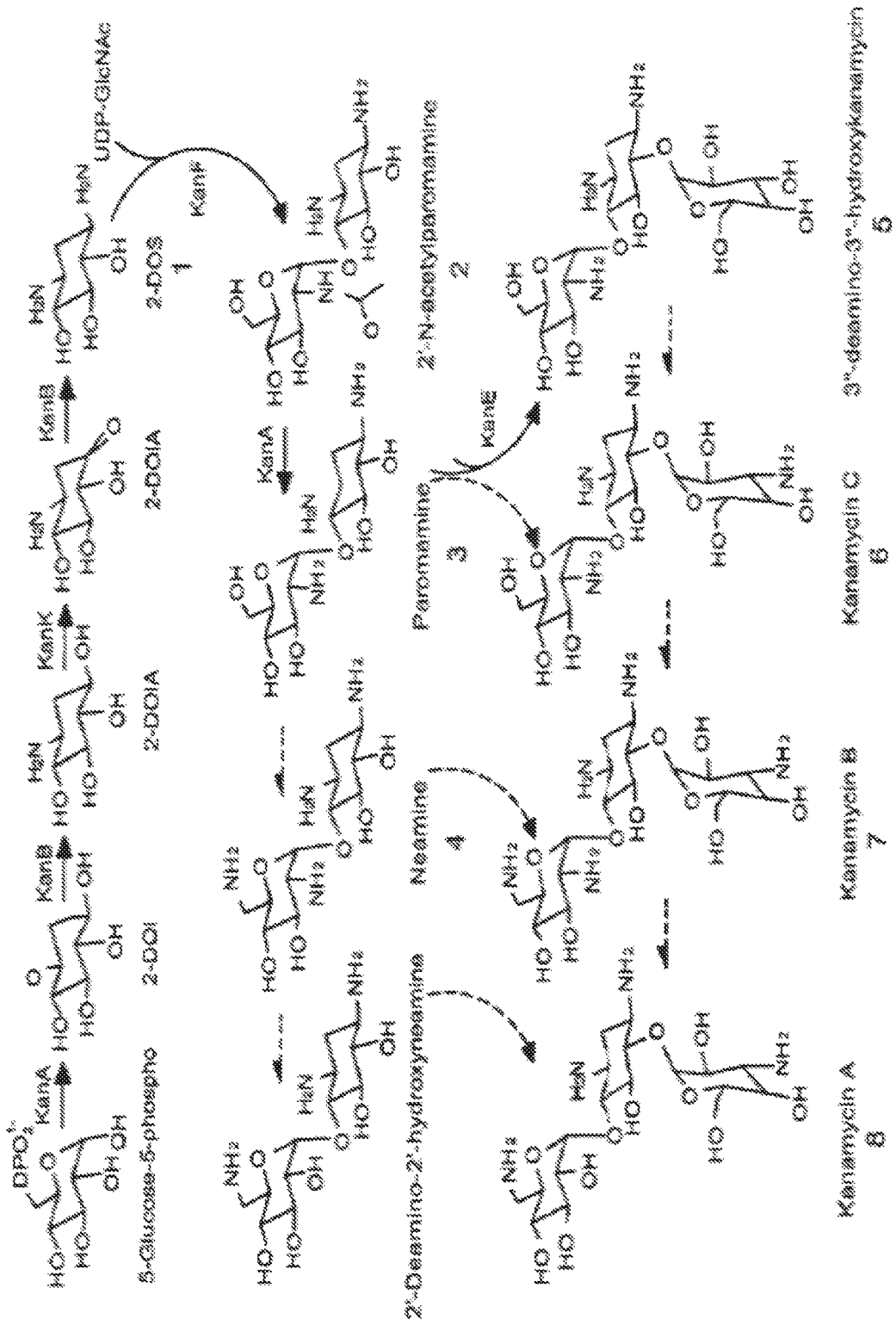
Figure 2A:
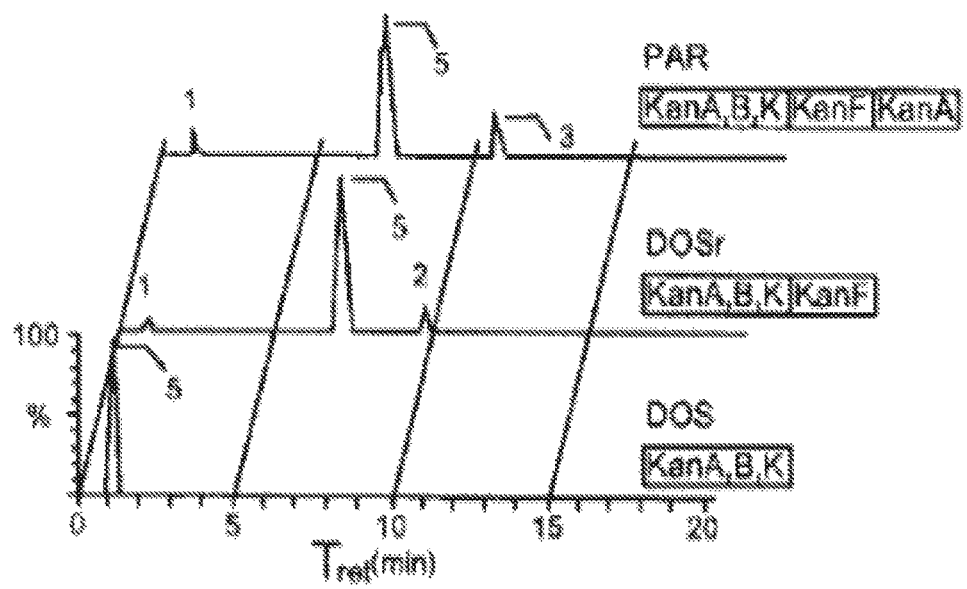
FIGS. 2A to 2H show the results of HPLC-ESI-MS anlysis of kanamycin biosynthetic intermediates obtained in vitro expression of putative kanamycin gene sets in recombinant *S. venezuelae* hosts and in vitro reactions using cell-free extracts of recombinants.

First, compound 3 was biosynthesized from Glc-6-phosphate as shown in FIG. 1B. As expected, the recombinant heterologous strain expressing kanA-kanB-kanK (DOS strain) produced compound 1 (21.4 µM) (FIG. 2A). To confer resistance to kanamycin in *S. venezuelae* without modifying the aminoglycoside structure, three resistance genes gtmF-gtmK-gtmL from the gentamicin gene cluster were introduced into the recombinant heterologous strain. Transformants expressing these genes were resistant to >10.0 mg/ml of the commercially available kanamycin compared to 1.0 µg/ml in control strains. These resistance genes were expressed together with the kanamycin biosynthetic genes in the heterologous host in subsequent experiments.

Figure 2B:
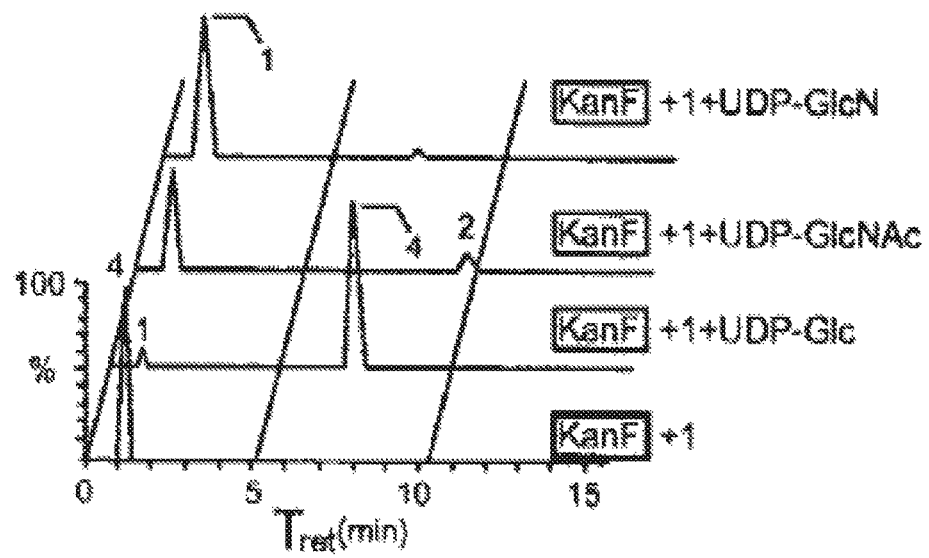

Compound 2 (1.3 µM) was produced by expressing DOS biosynthetic genes plus kanF encoding the first glycosyltransferase. Interestingly, a greater amount of compound 9 (7.1 µM) was produced at the same time. Moreover, The cell-free extract of *S. venezuelae* expressing kanF supplemented with compound 1 as a glycosyl acceptor and UDP-Glc or UDP-GlcNAc as a glycosyl donor produced 9-fold greater amount of compound 9 than that of compound 2 (FIG. 2B). Therefore, it indicates that KanF accepts both UDP-Glc and UDP-GlcNAc as cosubstrates but preferentially transfers UDP-Glc to compound 1. Compound 3 (2.2 µM) was produced by the recombinant strain (PAR strain) expressing kacA as 2'-N-acetylparomamine deacetylase together with compound 2/9 biosynthetic genes (FIG. 2A).

It is necessary to convert compound 3 into compound 4 for the kanamycin biosynthesis. It was estimated that KanI and KacL would participate in the conversion of compound 3 into compound 4 based on the in silico analysis of the aminoglycoside gene cluster. Meanwhile, it is considered that KanC and KanD are responsible for the formation of UDP-kns by aminating the C-3 hydroxyl group of UDP-Glc. Otherwise it is considered that KanC and KanD participate in the production of compound 6 from compound 5.

Figure 2C:
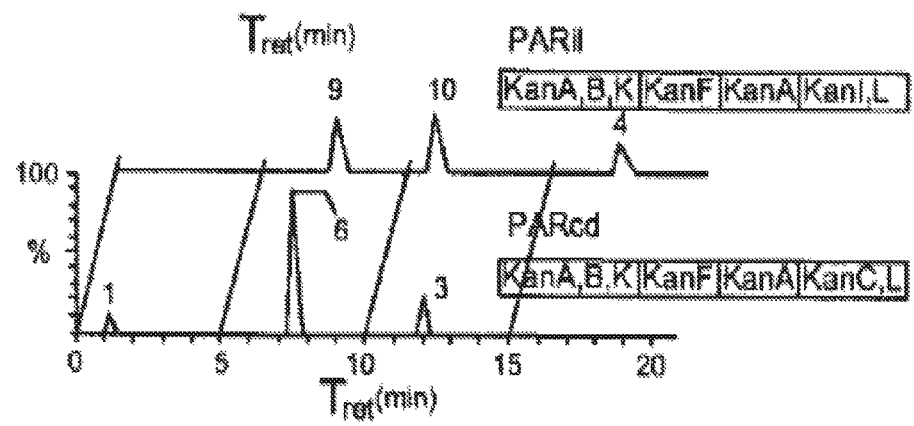
Figure 2D:
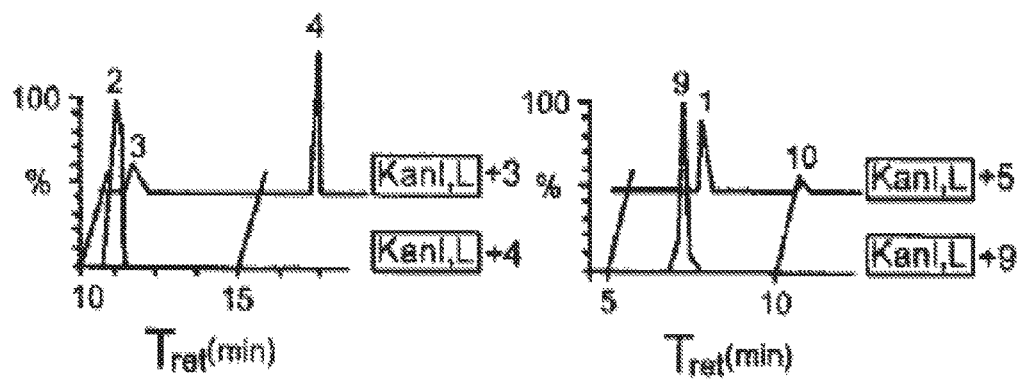

In one example of the present invention, kanC-kanD genes were first expressed in PAR strain (PARcd strain) to identify the functions of KanI-KacL and KanC-KanD. However, expression of kanC-kanD in the strain PAR (strain PARcd) produced only 3 and 9 (FIG. 2C), indicating that KanC-KanD does not participate in amination of the pseudodisaccharides. On the contrary, the recombinant strain (PARil strain) expressing kanI-kacL produced compound 10 (4.3 µM) as well as compound 4 (2.2 µM) (FIG. 2C). Incubation of the cell-free extracts of the recombinant expressing kanI-kacL with compounds 3 and 9 resulted in the production of compounds 4 and 10 (FIG. 2D).

Figure 2E:
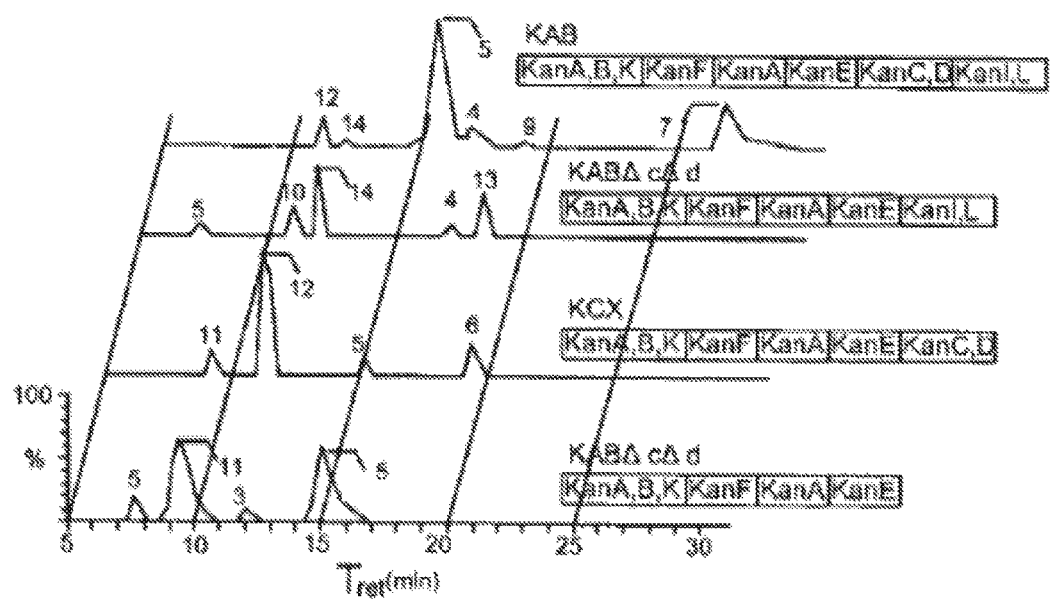

In one example of the present invention, pseudotrisaccharide kanamycins were biosynthesized. Compound 5 (3.2 µM) and compound 11 (4.5 µM), which was not known as a biosynthetic intermediate, were produced by the recombinant (KCXΔcΔd strain) expressing kanE encoding a second glycosyltransferase together with genes for biosysnthesis of compound 3/9 (FIG. 2E). Additional expression of kanC-kanD in KCXΔcΔd strain (KCX strain) resulted in the production of compound 6 (1.6 µM) and compound 12 (6.0 M), C-3" amination. The strain (KABΔcΔd strain) obtained by expressing kanI-kacL in KABAcAd strain produced compound 13 (2.0 µM) and compound 14 (3.2 µM). Moreover, the strain (KAB strain) obtained by expressing kanC-kanD in KABΔcΔd strain produced compound 7 of 1.0 mg/l (2.1 µM) and compound 8 of 3.1 mg/l (6.3 µM) (FIG. 2E).

Figure 2F:
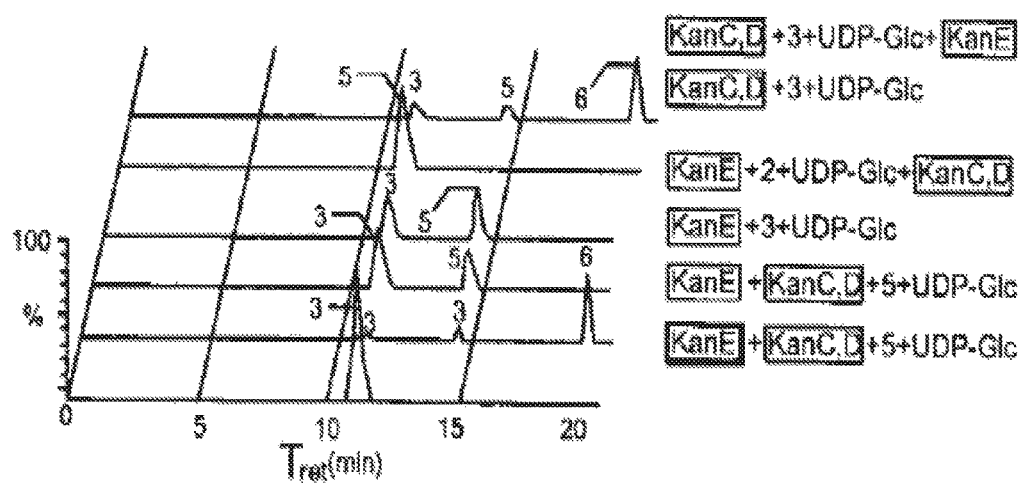
Figure 2G:
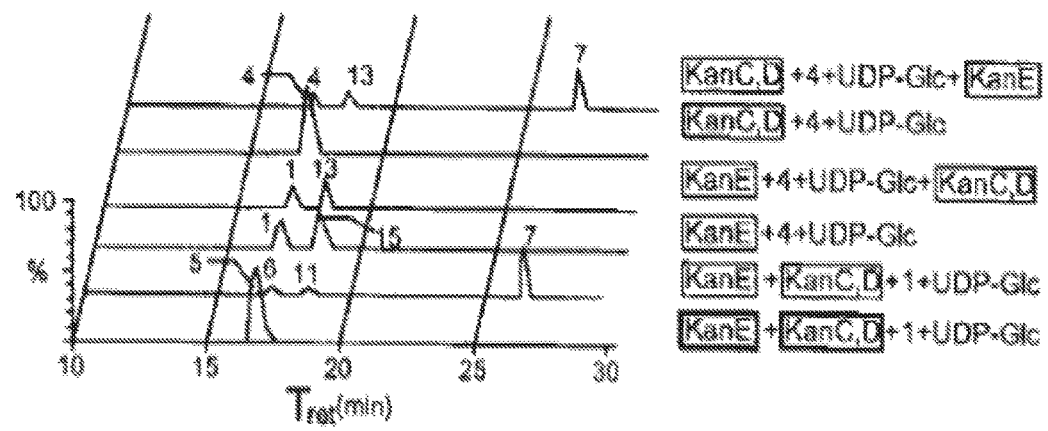

In one example of the present invention, cell-free extracts of recombinant *S. venezuelae* strains expressing kanE or kanC-kanD were prepared to determine whether UDP-kns biosynthesized from UDP-Glc is linked at the C-6 position of pseudodisaccharide or whether a Glc moiety of pseudodisaccharide is converted into kanosamine. Compounds 3 and 4 were incubated with UDP-Glc to produce compounds 5/6 and 13/7, respectively. When compounds 3 and 4 and UDP-Glc were added to the cell-free extracts of the recombinant strain expressing kanE, compounds 5 and 13 were produced, respectively. When these reactions were quenched and the resulting mixture was incubated together with the cell-free extracts of the strain expressing kanC-kanD, compounds 5 and 13 remained and further conversion was not observed. However, when compounds 3 and 4 were reacted with UDP-Glc and the cell-free extracts of the strain expressing kanC-kanD, compounds 6 and 7 were produced, respectively (FIGS. 2F and 2G). The same results were observed when compounds 9 and 10 were used as substrates (FIG. 6). These results showed that the hydroxyl group of UDP-Glc was aminated before the glycosyl transfer reaction by the enzyme pair during the biosynthesis of kanosamine. This example can be observed in the biosynthesis of kanosamine in *Amycolatopsis mediterranei*, a rifamycin-producing strain.

Figure 2H:
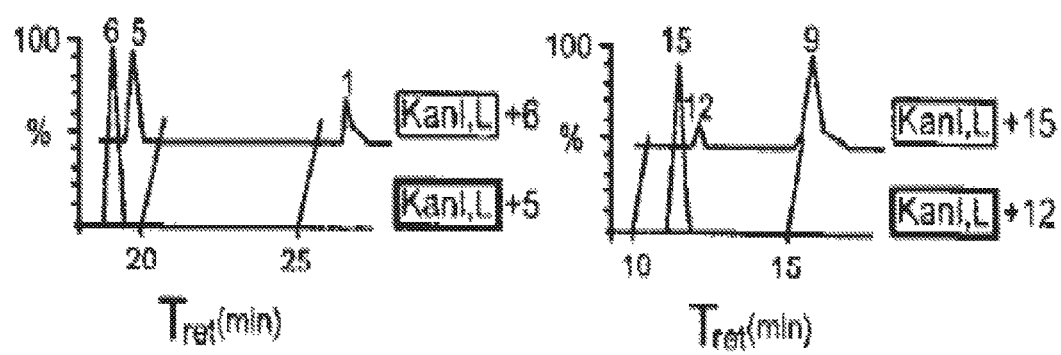
Figure 3:
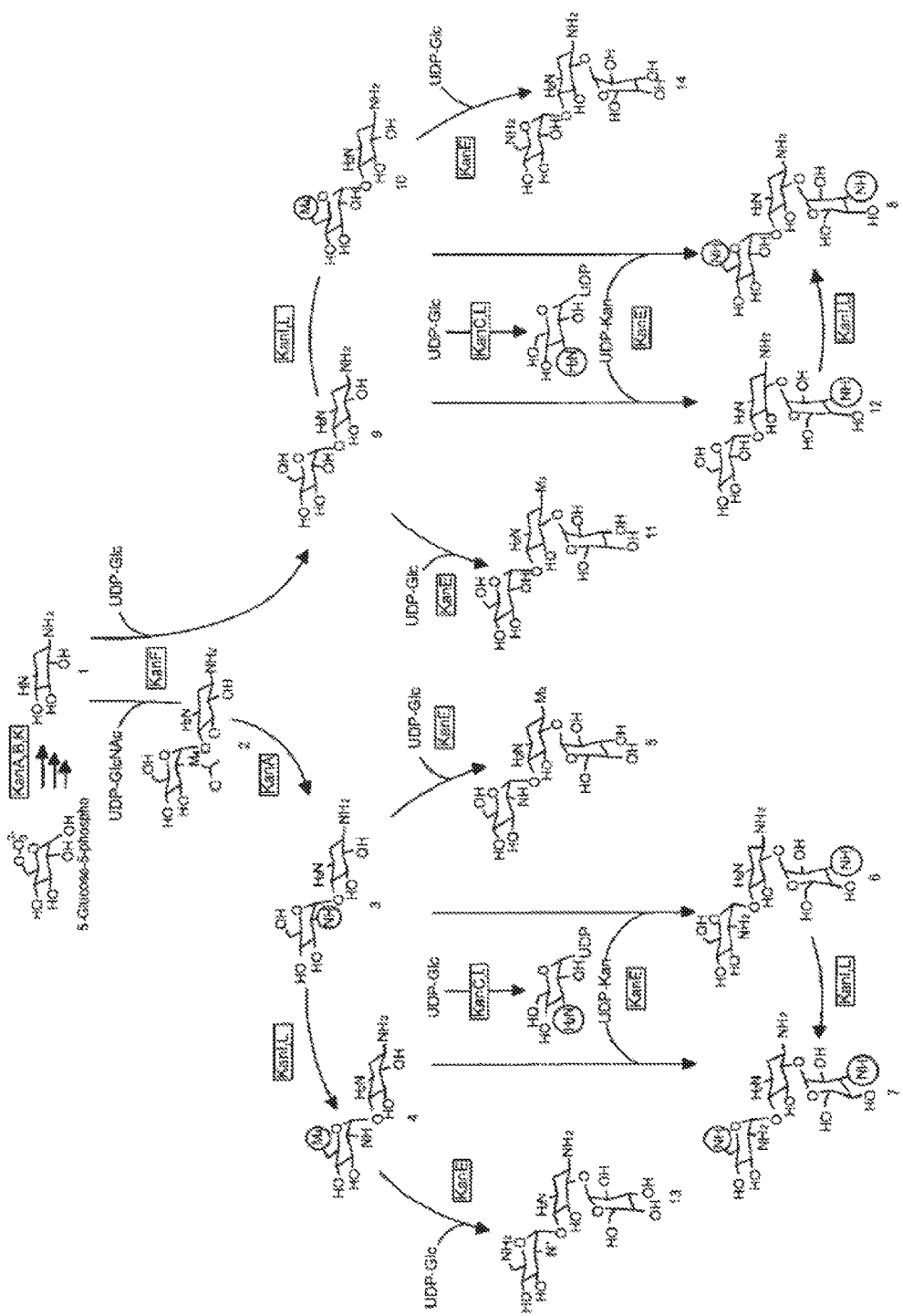
FIG. 3 shows a decalcomania-like kanamycin biosynthetic pathway, in which each colored block represents an annotated gene and its product has been proven to catalyze the biosynthesis of kanamycin intermediates. Each colored-circle represents the functional group formed by the product of the gene shown by the same colored block.

Moreover, when the cell-free extracts of the strain expressing kanI-kacL were incubated together with compounds 6 and 12, compounds 7 and 8 were produced, respectively. It is considered that KanI and KacL participate in the biosynthesis of compounds 4 and 10 as well as compounds 7 and 8 (FIGS. 2D and 2H), which shows their substrate flexibility toward pseudodi- and tri-saccharides. In summary, a decalcomania-like kanamycin biosynthetic pathway of the kanamycin complex dominated by KanF and KanE glycosyltransferases was identified (FIG. 3).

Figure 4A:
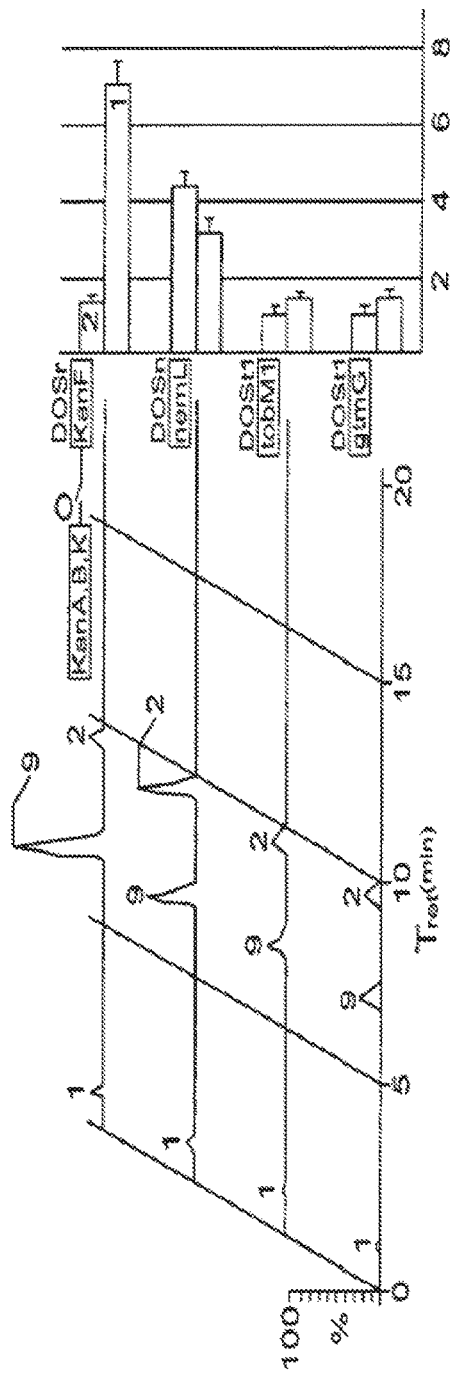
FIGS. 4A to 4C show the results of HPLC-ESI-MS/MS analysis of kanamycin biosynthetic intermediates obtained from the recombinant strains in which the first glycosyltransferase-encoding gene has been changed.

In one example of the present invention, the biosynthesis of kanamycin was modified. Compound 8 is the major fermentation product in both wild-type kanamycin producer *S. kanamyceticus* and the heterologous host *S. venezuelae*. It was shown that KanF glycosyltransferase preferred UDP-Glc to UDP-GlcNAc in the previous experiment. KanI-KacL, which preferred compound 12 to compound 6, was involved in the yield of compounds 8 and 7 (FIG. 2H). While amikacin (compound 15) can be synthesized from compound 8, the arbekacin, a latest semi-synthetic aminoglycoside having antibacterial activity against resistant bacteria, can be produced by removing the 3',4'-hydroxyl group followed by 1-N-acylation with AHBA. It was supposed that the biosynthesis of kanamycin tends to increase the yield of compound 7, if the kanF gene encoding the first glycosyltransferase was substituted with another gene encoding the glycosyltransferase which prefers UDP-GlcNAc to UDP-Glc as a glycosyl donor in the genetic construct for the biosynthesis of compounds 7 and 8. First, the inventors replaced kanF in the DOS strain with nemD, tobM1, and gtmG encoding three different glycosyltransferases from neomycin, tobramycin, and gentamicin. The DOSf strain as a control expressing kanF produced compound 2 (1.4 µM; 14% of the total pseudodisaccharide) and compound 9 (7.1 µM; 79%). On the contrary, the strain (DOSn strain) expressing nemD produced compound 2 (4.4 µM; 57%) and compound 9 (3.4 µM; 36%), from which it seemed that NemD use UDP-GlcNAc preferentially in contrast to KanF. When tobM1 and gtmG replaced kanF (DOSt$_1$ and DOSg strains), there was no significant change in the ratio of compounds 2 and 9 produced (FIG. 4A).

Figure 4B:
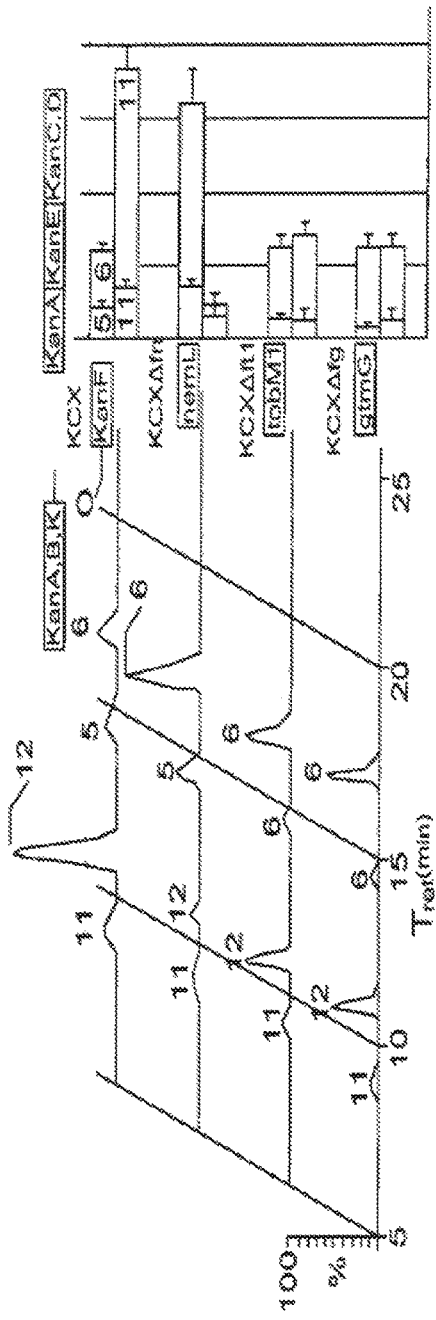
Figure 4C:
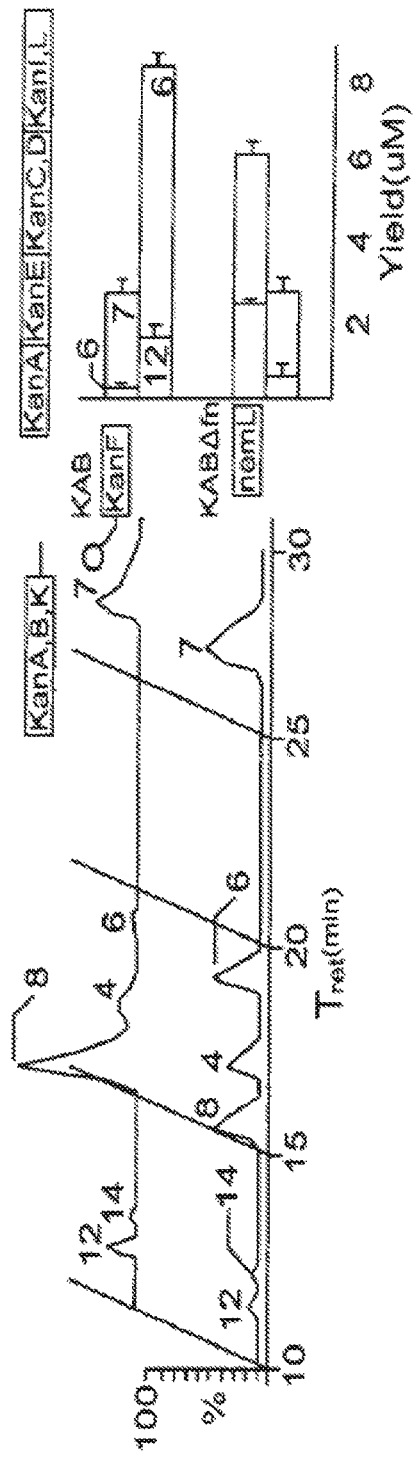

Moreover, in another example of the present invention, nemD, tobM1, and gtmG were separately substituted for kanF in KCX strain. When comparing the ratio of compounds 6 and 12 (1.6 µM, 16% and 6.0 µM, 60%) produced by KCX strain, the ratio of pseudodisaccharides 6 and 12 (5.0 µM, 65% and 0.4 µM, 7%) produced by the recombinant strain (KCXΔfn) expressing nemD was inverted. However, the ratio of pseudodisaccharide products 6 and 12 in the recombinant strain expressing either tobM1 (KCXΔft$_1$) or gtmG (KCXΔfg) were similar to each other (FIG. 4B). Moreover, while the yields of compounds 7 and 8 produced by KAB strain were 21% (2.3 μM) and 61% (6.8 μM), the yield of compound 7 in the strain (KABΔfn) obtained by substituting kanF with nemD was increased to 46% (FIG. 4C).

Figure 5A:
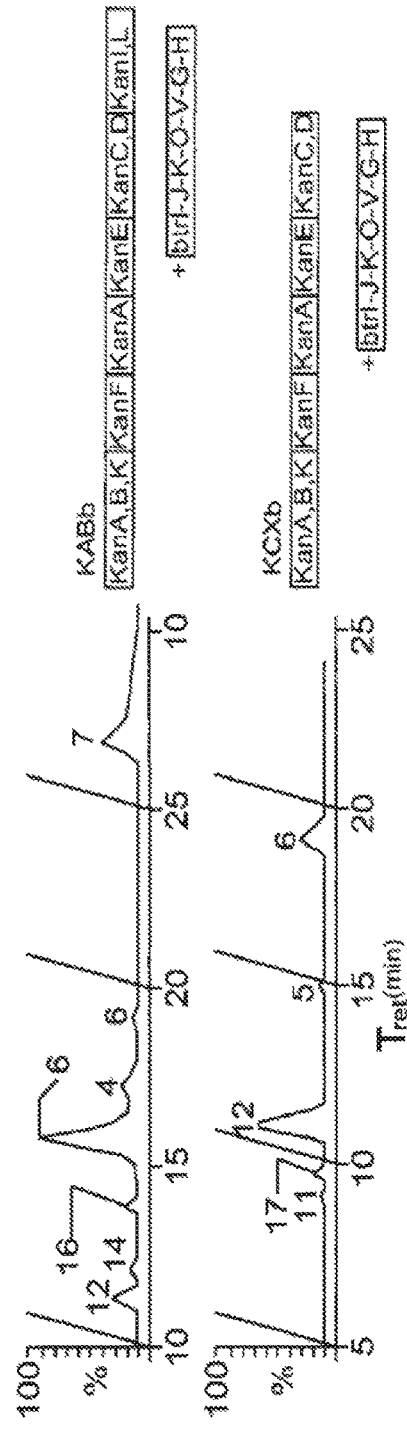
FIGS. 5A to 5C show the results of HPLC-ESI-MS/MS analysis of compounds 17, 19, and 20 produced by the recombinant strains.
Figure 5B:
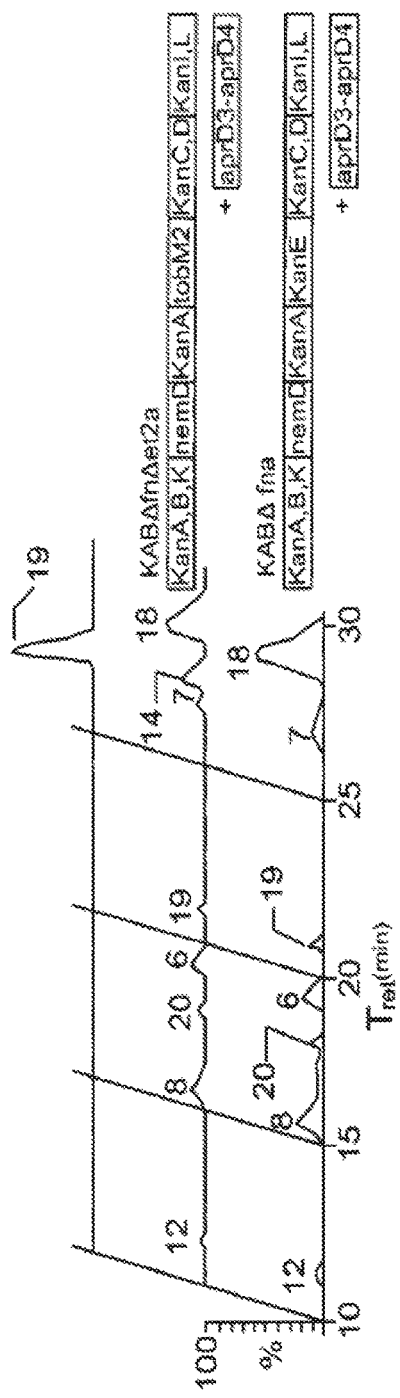
Figure 5C:
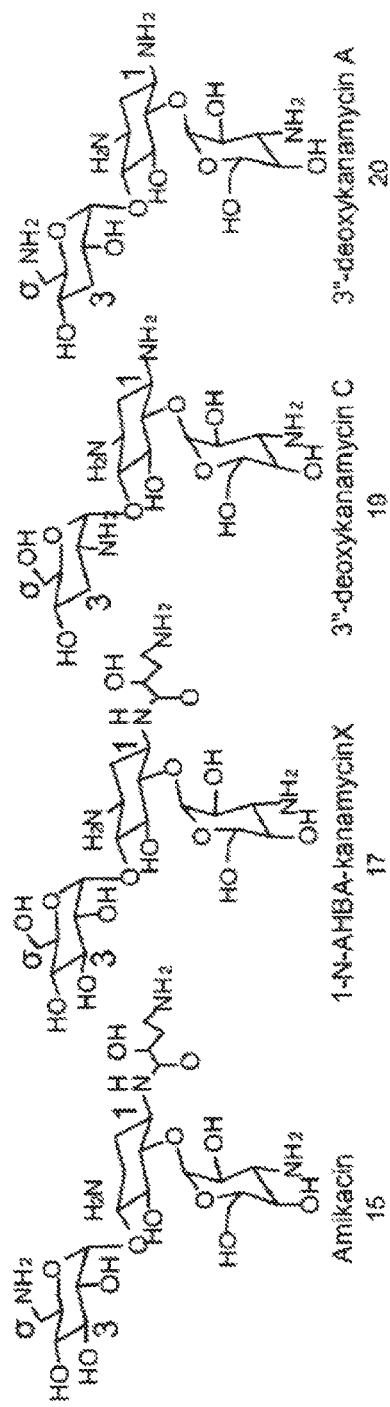

In another example of the present invention, 1-N-AHBA-kanamycin and 3'-deoxykanamycin were produced by direct fermentation. The inventors have modified the kanamycin biosynthetic pathway for in vivo production of 1-N-acylated kanamycin containing AHBA such as compound 15 and 3'-deoxykanamycin such as compound 16. The AHBA molecular structure was observed in the naturally-occurring butirosin. Recently, it has been reported that the btrG-btrH-btrI-btrf-btrK-btrO-btrV gene set is responsible for biosynthesis and introduction of the AHBA side chain into the amino group at C-1 of 2-DOS in butirosin. Compound 17 (0.6 mg/l, 1.0 μM), a new aminoglycoside compound, was produced by introducing these genes into the KCX strain. Moreover, 0.5 mg/1 (0.8 μM) of compound 15 was successfully produced by expressing the btr gene set in the KAB strain (FIGS. 5A and 5C).

Moreover, the inventors have analyzed the aminoglycoside gene cluster by bioinformatics analysis to find aprD3-aprD4, two putative apramycin genes, from *S. tenebrarius*, a tobramycin (compound 16)-producing strain. It seems that the aprD3-aprD4 genes are responsible for C-3' deoxygenation of pseudodi- and/or tri-saccharides.

In one example of the present invention, the aprD3-aprD4 genes were introduced into KABΔfn engineered for the increased production of compound 7. The resulting strain KABΔfna produced compound 18 as a major product and produced compounds 19 and 20 but did not produce compound 16 (FIGS. 5B and 5C). This result shows that the activity of AprD3-AprD4 pair removes the 3'-hydroxyl group in compounds 3, 10, and 4. It also indicates the second glycosyltransferase KanE selectively transfers kanosamine to compounds 3 and 10 but not to compound 18. To select the glycosyltransferase that transfers kanosamine to compound 18 to produce compound 16, cell-free extracts of *S. kanamyceticus* and *S. tenebrarius* were prepared and incubated together with compound 18. The cell-free extract of *S. tenebrarius* containing tobM2 as a second glycosyltransferase encoding gene converted compound 18 into compound 16, but the cell-free extract of *S. kanamyceticus* did not (FIG. 7). Therefore, the inventor have constructed the glycosyltransferase encoding genes nemD, tobM2, and aprD3-aprD4 and a new strain (KABΔfnΔet$_2$a) expressing compound 7 biosynthetic gene and produced compound 16 (0.4 mg/1, 0.8 μM) (FIGS. 5B and 5C). The cell-free extracts of the strain expressing aprD3-aprD4 converted compound 4 into compound 18, but did not convert compound 7 into compound 16, which means that these enzymes are active only to pseudodisaccharides (FIG. 7).

In one embodiment of the present invention, antibacterial spectra against kanamycin intermediates and analogs produced by the present invention were measured. Typical gram-negative strains (*E. coli* and *Pseudomonas aeruginosa*) and four clinically isolated strains were employed to check the antibacterial spectra (See table 2).

Among the pseudodisaccharides, the 6'-amino compounds 4 and 10 were more active than the 6'-hydroxy derivatives 3 and 9 against kanamycin-sensitive *E. coli* strains. Compared with compounds 6 and 12 containing 6'-hydroxy group, their 6'-amino counterparts 7 and 8 were more active against kanamycin-sensitive test strains. In addition, the 3"-amino compounds 6, 7, 8, and 12 showed increased activity against the test strains when compared with the corresponding 3"-hydroxy derivatives 5, 13, 14, and 11. Therefore, when C-6' and/or C-3" hydroxyl group of kanamycin were aminated, the antibacterial activity was increased, which was consistent with the previous study.

In the test with the clinically isolated amikacin-sensitive *P. aeruginosa* strain, most kanamycin intermediates showed very low antibacterial with exception of the compounds 6, 7, 8, and 12. Interestingly, new compound 17 showed improved antibacterial activity against all the test strains compared with amikacin (compound 15). Especially, compound 15 showed no activity on the clinically isolated amikacin-resistant *P. aeruginosa* strain, whereas, compound 17 showed very strong activity (MIC ~64).

TABLE 2

| | | Antibacterial spectra against Gram-negative bacteria | | | | | |
|---|---|---|---|---|---|---|---|
| | | MIC (μg/ml) | | | | | |
| | | Typical strains | | Clinically isolated strains | | | |
| Kanamycin-relatedamino-glycosides | | *E. coli* ATCC 25922(Kan$^S$) | *P. aeruginosa* ATCC 27853(Kan$^R$) | *E. coli* CCARM 1A020(Kan$^S$) | *E. coli* CCARM 1A023(Kan$^R$) | *P. aeruginosa* CCARM 2206(Amk$^S$) | *P. aeruginosa* CCARM 2178(Amk$^R$) |
| Pseudo-disaccharides | 3 | 128 | NA | 128 | NA | NA | NA |
| | 9 | 128 | NA | 128 | NA | NA | NA |
| | 4 | 64 | NA | 64 | NA | 128 | NA |
| | 10 | 64 | NA | 64 | NA | 128 | NA |
| Pseudo-trisaccharides | 6 | 16 | NA | 16 | NA | 64 | NA |
| | 12 | 16 | NA | 16 | NA | 64 | NA |
| | 5 | 128 | NA | NA | NA | NA | NA |
| | 11 | NA | NA | NA | NA | NA | NA |
| | 7 | 2 | NA | 4 | NA | 32 | NA |
| | 8 | 2 | NA | 4 | NA | 16 | NA |
| | 13 | 128 | NA | 128 | NA | NA | NA |
| | 14 | 128 | NA | 128 | NA | NA | NA |
| AHBA-pseudo-trisaccharides | 15 | 128 | 64 | 128 | 32 | ≤0.25 | NA |
| | 17 | 16 | 16 | 32 | 16 | 0.25 | 64 |

MIC: minimum inhibitory concentration. Type strains and clinically isolated strains were obtained from ATCC (American Type Culture Collection, USA) and CCARM (Culture Collection of Antimicrobial Resistant Microbes, Republic of Korea), respectively.
Kan$^S$ and Kan$^R$ represent the kanamycin-sensitive strain and the kanamycin-resistant strain, respectively. Amk$^S$ and Amk$^R$ represent the amikacin-sensitive strain and the amikacin-resistant strain, respectively.
NA represents no activity at 128 μg/mL.

The inventors have constructed 3D models of glycosyltransferases such as KanF and NemD. The 3D models were generated by homology modeling using the crystal structure of the MshA as a template. These enzymes shared over 40% overall sequence similarity, respectively. Critical residues and their interactions were preserved in both strongly supporting conserved catalytic association mechanisms.

To gain insight into the catalytic mechanism, the simulations aimed at the preparation of KanF/NemD complex with glycosyl-donors/acceptor were repeated. First, the inventors performed a docking of the glycosyl-donors (UDP-Glc and UDP-GlcNAc) to the putative substrate binding site in both glycosyltransferases KanF and NemD using AutoDock, respectively. Secondly, the glycosyl-acceptor (compound 1) was docked into the putative glycosyl-acceptor binding site of each glycosyltransferase/glycosyl-donors complex using CDOCKER and deeply docked into the Glc or GlcNAc area, thus making ideal interactions with their glycosyl-donors and the surrounding residues of each glycosyltransferase.

The distance between the C1 atom of the glycosyl-donors and O3 atom of compound 1 fluctuated only within very narrow limits (~3.0 Å). The total energy of the [KanF or NemD/glycosyl-donors/compound 1] complex was stabilized and remained stable during the simulation. The radius of gyration for the complexes was found to be stable at roughly 20 Å throughout the simulation, suggesting that the presence of compound 1 in the complexes induce the protein to adopt more compact form compared to the proteins in the absence of compound 1. There is a large hydrophilic pocket between two domains of glycosyltransferase KanF (or NemD). The pocket is formed by glycosyl-donor neighboring hydrophilic residues such as Glu14 (Glu41), Gln19 (Gln46), Gln20 (Gln47), His88 (His115), Tyr110 (Tyr137), Thr111 (Thr138), Asp117 (Asp204), Lys218 (Lys245), Asn272 (Asn299), Glu292 (Glu319), Glu293 (Glu320), Ser297 (Ser324), and Glu300 (Glu327). Analysis of hydrophilic-hydrophilic contact in the docked structure showed that these residues are playing a crucial role in the interaction. The sugar groups of glycosyl-donors/compound 1 would interact with hydrophilic residues of the binding pocket. The uracil moiety of both glycosyl-donors forms hydrophobic interactions with Gly243 (Gly270), Phe269 (Phe296), and Ile275 (Ile302), whereas their ribose moieties build the hydrophilic interactions with Ser297 (Ser324), and Glu300 (Glu327). The hydrophilic contact between compound 1 and Tyr110 (Tyr137) is strong because the phenolic group of Tyr is moved somewhat inward or outward from its original position as compound 1 which is located above the phenolic group tries to get closer to Tyr110 (Tyr137). However, Leu89 (Leu116) make a strong hydrophobic interaction with compound 1 which doesn't move much at all. The amino group at C3 position in compound 1 interacts with the Asp177 (Asp204) which allows the dissipation of the delocalized negative charge of compound 1. The hydroxyl group at C6 position in compound 1 make hydrophilic interactions with His88 (His115), whereas the ring moiety of compound 1 makes hydrophobic interactions with Gly16 (Gly43) and Val17 (Val44). The Glc or GlcNAc part in the glycosyl-donor is anchored to a pocket formed by Glu292 (Glu319), Glu293 (Glu320), and Leu294 (Leu321), proposing that these residues might play a critical role in the stability of those complexes. The sugar parts of glycosyl-donors stack against between the carboxyl moieties of Glu292 (Glu319) and Glu293 (Glu320). Leu294 (Leu321) is located at almost the center of hydrophobic and hydrophilic interaction with sugar moiety.

The inventors have performed the molecular dynamics and binding free energy analysis. The glycosyl-donors have several hydrophilic groups as described above, thus their hydrogen bond interaction with glycosyltransferases as well as solvent molecules at the active site is important for them to bind tightly with both KanF and NemD. The number of hydrogen bonds between KanF and UDP-Glc (~5) is larger than that between KanF and UDP-GlcNAc (~2), whereas the number between NemD and UDP-Glc (~3) is smaller than that between NemD and UDP-GlcNAc (~6), indicating that UDP-Glc binds more tightly to KanF than does UDP-GlcNAc to NemD.

The calculated free energies of UDP-Glc and UDP-GlcNAc binding to KanF and NemD is −42.2, −47.3, −41.4, and −46.7 kJ/mol, respectively (See table 3).

TABLE 3

Average binding free energies(kJ/mol) between glycosyl-donors and surrounding residues of KanF and NemD during molecular dynamics simulation.

| | KanF + UDP-GlcNAc | KanF + UDP-Glc | NemD + UDP-Glc | NemD + UDP-GlcNAc |
|---|---|---|---|---|
| $\langle E \frac{vdW}{enz} \rangle$ | −7.98 ± 0.59 | −7.13 ± 0.17 | −8.07 ± 0.24 | −7.45 ± 0.40 |
| $\langle E \frac{vdW}{enz + sub} \rangle$ | −42.09 ± 0.39 | −35.04 ± 0.84 | −43.90 ± 0.38 | −41.95 ± 0.08 |
| $\langle E \frac{Elec}{enz} \rangle$ | −258.33 ± 1.65 | −284.48 ± 1.47 | −253.13 ± 1.34 | −277.01 ± 1.83 |
| $\langle E \frac{vdW}{enz} \rangle$ | −329.18 ± 0.47 | −367.88 ± 0.48 | −321.53 ± 0.74 | −356.63 ± 0.18 |
| $\langle E \frac{vdW}{enz + sub} \rangle$ | −42.25 ± 1.15 | −47.28 ± 1.82 | −41.37 ± 1.18 | −46.71 ± 1.09 |

The binding free energy (ΔG)) calculation was based on the molecular dynamics simulation;

$$\Delta G = 0.2 \left( \left\langle E \frac{vdW}{enz - sub} \right\rangle - \left\langle E \frac{vdW}{enz} \right\rangle \right) - 0.5 \left( \left\langle E \frac{Elec}{enz - sub} \right\rangle - \left\langle E \frac{Elec}{enz} \right\rangle \right)$$

wherein < > denotes averages of the van der Waals (wdW) and electrostatic (Elec) interactions between the substrate (sub) such as UDP-Glc and its surrounding residues in enzymes (enz) such as KanF and NemD. 0.2 and 0.5 are scaling factor for wdW and Elec, respectively.

The inventors have discovered that the substrate-flexible glycosyltransferase KanF synthesizes compounds 9 and 2 by taking both UDP-Glc and UDP-GlcNAc as cosubstrates for attachment to compound 1. The discovery of the structure of compound 9 indicated that KanF is a glucose transferase as well as an N-acetylglucosamine transferase. The activity of this glycosyltransferase has not been known in the biosynthesis of aminoglycoside. Moreover, compound 9 is converted into compound 10 in the same way as compound 3 is converted into compound 4 by KanI-KacL. KanI-KacL also convert compounds 6 and 12 into compounds 7 and 8, respectively. The second glycosyltransferase KanE also shows remarkable substrate flexibility toward the glycosyl-acceptor and produces compounds 6, 7, 12, and 8, respectively by transferring UDP-Kns to compounds 3, 4, 9, and 10. KanE also takes UDP-Glc as the glycosyl-donor and transfers UDP-Glc to the pseudodisaccharide, thereby producing compounds 5, 13, 11, and 14 (FIGS. 2 and 3).

The method of directly producing AHBA-binding kanamycin using the recombinant strain of the present invention is first discussed as the direct fermentative production of the semi-synthetic aminoglycoside.

Moreover, compound 17 (1-N-AHBA-kanamycin X) as a new aminoglycoside compound produced by the present invention has strong antibacterial activity against all kanamycin and amikacin-resistant test strains. The unique structural difference between compound 15 and 17 is a functional group attached at C-6' position (FIG. 5C), which indicates that compound 17 is active against bacteria having resistance to compound 15 by removing the 6-amino group which acts as a target of aminoglycoside 6-acetyltransferase. Another advantage of compound 17 is the reduced toxicity due to the reduction in the number of amino groups.

Furthermore, the in vivo production of compound 16 by a modified pathway is more economical than the conventional method using hydrolysis of 6"-O-carbamoyltobramycin which occupies 9% of the total nebramycin factors produced by S. tenebrarius.

MODE FOR THE INVENTION

Hereinafter, the present invention will be described by way of examples in detail. However, the following examples are provided to facilitate the understanding of the present invention, and the present invention is not limited to or by the following examples.

EXAMPLE 1

Preparation of Materials

Standard kanamycin, kanamycin B, neomycin, paromomycin, tobramycin, and amikacin were purchased from Sigma (USA). 2-mercaptoethanol, phenylmethyl-sulfonyl fluoride (PMSF), phenol/chloroform/isoamyl alcohol (25:24:1), uridine 5'-diphospho-D-glucose (UDP-Glc), and glass beads (150 to 212 µm) were also purchased from Sigma. Heptafluorobutyric acid (HFBA) was obtained from Fluka, and HPLC-grade acetonitrile, methanol, and water were obtained from J. T. Baker. 2-deoxystreptamine (2-DOS, compound 1) and UDP-2-N-acetyl-D-glucosamine (UDP-GlcNAc) were purchased from GeneChem (Republic of Korea). Cation solid-phase exchanger (OASIS MXC SPE, 3 mL/60 mg) and vacuum manifold were purchased from Waters. The culture medium components, soybean meal, yeast extract, and malt extract were acquired from BD Science (USA).

Paromamine and neamine were prepared from paromomycin and neomycin, respectively, by methanolysis. UDP-2-D-glucosamine (UDP-GlcN) was prepared by enzymatic reaction of UDP-D-glucose pyrophosphorylase with glucosamine-1-phosphate and uridine 5'-triphosphate (UTP). Escherichia coli DH10B and plasmid Litmus 28 (New England Biolabs) were used for routine subcloning. High-copy number E. coli-Streptomyces shuttle vector pSE34 containing the strong ermE* promoter plus a thiostrepton resistance marker was used as an expression plasmid.

EXAMPLE 2

Culture of Strains

The recombinant strains of S. venezuelae were grown in liquid R2YE at 30° C. for preparation of protoplasts, which were regenerated on R2YE agar medium supplemented with thiostrepton (30 µg/ml). The E. coli strains used for subcloning were grown in LB medium supplemented with ampicillin (50 µg/ml) to select for plasmids.

For production of kanamycin biosynthetic intermediates and their analogs, S. venezuelae strains expressing the biosynthetic candidate genes were cultivated at 30° C. for 4 days in one liter of baffled Erlenmeyer flasks containing 300 mL of R2YE medium supplemented with thiostrepton (25 µg/ml). S. kanamyceticus ATCC 12853 was grown at 30° C. for 5 days in liquid ISP2 (0.4% yeast extract, 1.0% malt extract, and 0.4% glucose), and S. tenebrarius ATCC 17920 was grown at 30° C. for 5 days in fermentation medium (2.0% glucose, 2.0% soluble starch, 4.0% soybean meal, 0.5% yeast extract, 0.5% CaCO$_3$, and 0.4% MgSO$_4$7 H$_2$O, pH 7.0).

To check the antibacterial spectra of kanamycin biosynthetic intermediates and their analogs, a total six kinds of Gram-negative bacteria such as kanamycin-sensitive (Kan$^S$) E. coli ATCC 25922, kanamycin-resistant (Kan$^R$) Pseudomonas aeruginosa ATCC 27853, Kan$^S$ E. coli CCARM (Culture Collection of Antimicrobial Resistant Microbes, Korea) 1A020, Kan$^R$ E. coli CCARM 1A023, amikacin-sensitive (Amk$^S$) P. aeruginosa CCARM 2206, and amikacin-resistance (Amk$^R$) P. aeruginosa CCARM 2178 were used.

EXAMPLE 3

Cloning and Construction of Expression Plasmids and Recombinant S. venezuelae Strains An engineered strain of S. venezuelae, which is deficient in biosynthesis of the endogenous deoxysugar thymidine 5'-diphospho (TDP)-D-desosamine, was used as a heterologous host. A gene replacement plasmid, pYJ188, was introduced into protoplasts of S. venezuelae YJO03 mutant for deletion of the kanamycin modifying gene (aphII) by a replicative plasmid-mediated homologous recombination. Several double crossover mutants were identified on the basis of their phenotypes of kanamycin sensitivity and their genotypes by Southern hybridization.

DNA fragments containing a variety of kanamycin biosynthetic genes were amplified from pSKC2 by PCR with specific deoxyoligonucleotide primers (See table 1). The DNA fragments encoding NemD, GtmG, AprD3, AprD4, TobM1, and TobM2 were obtained by PCR-amplification using genomic DNA of S. fradiae ATCC 10745, Micromonospora echinospora ATCC 15385, and S. tenebrarius ATCC 17920, respectively. DNA fragments containing btrI, btrJ, btrK, btrO, btrV, btrG, and btrH required for S-4-amino-2-hydroxybutyric acid (AHBA) biosynthesis and transfer were PCR-amplified using genomic DNA of Bacillus circulans NR3312 as a template. Each pair of primers contained several restriction sites to facilitate subcloning of each DNA fragment.

PCR was performed using Pfu polymerase (Fermentas) under the manufacturer's recommended conditions. All PCR products were cloned into Litmus 28 and sequenced to confirm their authenticity.

For expression of 2-DOS biosynthetic genes, PCR-amplified fragments containing kanA-kanB and kanK were digested with BamHI/SpeI and XbaI/HindIII, respectively, and simultaneously ligated with pSE34 which had been cut with BamHI and HindIII, thus generating pDOS. Plasmid pDOSf (kanA-kanB-kanK-kanF-gtmF-gtmK-gtmL) was constructed to express kanF along with 2-DOS biosynthetic genes by ligating the SpeII HindIII-digested DNA fragment of kanF with the XbaI/HindIII fragments of resistance gene set (gtmF-gtmK-gtmL) isolated from pYJ489, and inserting into pDOS as an XbaI/HindIII fragment.

All subsequent cloning steps for construction of plasmids pPAR, pPARcd, pPARi1, pKCXΔcΔd, pKCX, pKABΔcΔd, pKAB, pDOSn, pDOSt$_1$, pDOSg, pKCXΔfn, pKCXΔft$_1$, pKCXΔfg, and pKABΔfn were performed using the compatible cohesive ends of SpeI and XbaI sites.

For the direct fermentative production of 1-N-AHBA kanamycins, plasmid Litmus 28 containing btrG-btrH was digested by SpeI/SnaBI and ligated with the DNA fragment btrI-btrJ that had been cut by XbaI/SnaBI. The resulting plasmid carrying btrG-btrH-btrI-btrJ was subsequently ligated with the DNA fragment containing btrK-btrO-btrV in the same manner. Then, the plasmid containing btrG-btrH-btrI-bta-btrK-btrO-btrV was digested by XbaI/SpeI and transplanted into the XbaI site of pKCX and pKAB (See table 2) to generate pKCXb and pKABb, respectively. The correct orientations of the DNA fragments containing btrG-btrH-btrI-bta-btrK-btrO-btrV in the pKCXb and pKABb were confirmed by restriction fragment analyses.

Next, plasmid pKABΔfna and pKABΔfnΔet$_2$a were constructed in attempt to produce 3'-deoxykanamycins in vivo. The plasmid Litmus 28 containing aprD3 was digested by SpeI/HindIII and combined with the XbaI/HindIII DNA fragment containing aprD4. The plasmid containing aprD3-aprD4 gene set was ligated with the XbaI/HindIII DNA fragments containing nemD-kanE-kanC-kanD-kanI-kacA-kacL-gtmF-gtmK-gtmL. The resulting plasmid was moved into the XbaI/HindIII sites of pSE34 containing kanA-kanB-kanK (pDOS) to generate pKAB fna. Plasmid pKABΔfnΔet$_2$a was equivalent to pKABΔfna supplemented with tobM2 instead of kanE.

To prepare the cell-free extract of S. venezuelae for functional assignment of each kanamycin biosynthetic gene products, DNA fragments containing kanF, kanE, kanI-kacL, kanC-kanD, and aprD3-aprD4 were transplanted into pSE34 as XbaI/HindIII fragments, thus generating pKanF, pKanE, pKanI-KacL, pKanC-KanD, and pAprD3-AprD4, respectively. All resulting plasmids were then transformed into an engineered strain of S. venezuelae, thus yielding the corresponding recombinants.

EXAMPLE 4

Isolation and Identification of Kanamycin Biosynthetic Intermediates and their Analogs HPLC was performed with a Spherisorb S5 ODS2 (250× 20 mm, Waters) semi-prep column on the products of engineered recombinant strains in Example 3. The products were eluted with the same mobile phase used in HPLC-ESI-MS/MS analysis at a flow rate of 12 mL/min over a period of 150 min. The resulting eluent was fractionated into 3-mL portions that were monitored by HPLC-ESI-MS/MS to detect and characterize the presence of each kanamycin-related biosynthetic intermediate and analog. Fractions containing products of interest were pooled and extracted using OASIS MCX SPE followed by freeze-drying. $^1$H, $^{13}$C, and 2D $^1$H-$^1$H COSY NMR spectra were acquired using a Varian INOVA 500 spectrometer at 298 K. Chemical shifts were reported in ppm using trimethylsilyl-2,2,3,3-tetradeuteropropionic acid (TSP) as an internal reference. The assignment of each compound was carried out by comparison with previously assigned $^1$H and $^{13}$C NMR spectra, and NMR data processing was done using MESTREC (Magnetic Resonance Companion) software.

EXAMPLE 5

Analysis of Kanamycin Biosynthetic Intermediates and Analogs

Kanamycin biosynthetic intermediates and their analogs produced by recombinant S. venezuelae strains expressing aminoglycoside biosynthetic genes were extracted from the fermentation medium using the OASIS MCX (Waters) SPE cleanup procedure and analyzed by HPLC-ESI-MS/MS.

Analytical HPLC-ESI-MS/MS was performed on the analytes in an XTerra MS C$_{18}$ column (50×2.1 mm, 3.5 µm, Waters). The analytes were eluted with acetonitrile and 10 mM heptafluorobutyric acid (Fluka) for 45 minutes. Quantification of the analytes was conducted using MS/MS in the multiple reactions monitoring mode. This was done by selecting the two mass ions set to detect a transition of the parent ion to the product ion specific to the selected analytes: compound 1, 163>84; compound 2, 366>163; compounds 3 and 10, 324>163; compound 4, 323>163; compounds 5, 12 and 14, 486>163; compounds 6, 8 and 13, 485>163; compound 7, 484>163; compound 9, 325>163; compound 11, 487>163; compound 15, 586>264; compound 16, 468>163; compound 17, 587>264; compound 18, 307>163; and compounds 19 and 20, 469>163. Three separate cultivations and extractions were performed.

EXAMPLE 6

In Vitro Reactions to Analyze AprD3-AprD4 Activity

In vitro reactions to analyze the activity of AprD3-AprD4 pair on 3'-deoxygenation in the pseudodi- or tri-saccharide were carried out by supplementing 100 µM neamine or kanamycin B with the cell-free extracts from the recombinant host expressing aprD3-aprD4. After incubation at 30° C. for 2 hours, the reaction was quenched. The resulting supernatant containing the product of interest was extracted using OASIS MCX SPE, and then subjected to HPLC-ESI-MS/MS analysis. Independent experiments were carried out in duplicate, and the results are shown in FIG. 7.

EXAMPLE 7

In Vitro Reactions to Analyze Glycosyltransfer Activity of KanF

Cell-free extracts of S. venezuelae were prepared by glass-bead homogenization. These cell-free extracts were suspended in a Tris buffer solution containing 100 mM TrisHCl (pH 7.6), 10 mM MgCl$_2$, 6 mM 2-mercaptoethanol and 1 mM phenylmethyl-sulfonyl fluoride (PMSF, Sigma), and each protein concentration was calibrated. The glycosyltransfer reaction by KanF was initiated by supplementing 100 µM 2-DOS together with 200 M UDP-Glc (Sigma), UDP-GlcNAc (GeneChem), or UDP-GlcN as cosubstrates to the cell-free extracts of the recombinant host expressing only kanF. 100 µM 6'-hydroxy pseudodi- and tri-saccharides 3, 6, 9, and 12 were mixed with the cell-free extracts of the recombinant host expressing kanI-kacL to measure the activity of KanI-KacL for C-6'-amination. The resulting cell-free extracts were incubated at 30° C. for 2 hours before quenching with ice-cold phenol/chloroform/isoamyl alcohol (25:24:1, Sigma) and then subjected to centrifugation at 18,000 g for 5 minutes. The supernatant containing the product of interest was extracted using OASIS MCX SPE, mixed with 100 µM water, and then subjected to HPLC-ESI-MS/MS analysis.

EXAMPLE 8

In Vitro Reactions to Analyze KanC-KanD Activity

In vitro reactions to analyze the activity of KanC-KanD were carried out using cell-free extracts of two S. venezuelae strains expressing kanE or kanC-kanD. 200 µM UDP-Glc and 100 µM compound 3 or 4 were mixed with the cell-free extracts of the strains expressing kanE (or kanC-kanD) and incubated under the same conditions as Example 7 before quenching the reactions. After the resulting supernatant containing the product of interest was incubated together with the cell-free extracts of the strains expressing kanC-kanD (or kanE) at 30° C. for 2 hours, the reaction was quenched. The resulting supernatant was extracted in the above manner and then subjected to HPLC-ESI-MS/MS analysis.

EXAMPLE 9

In Vitro Reactions Using Cell-free Extracts from Wild-type Strains of S. kanamyceticus and S. tenebrarius In vitro reactions to determine the glycosyltransfer activities of KanE from S. kanamyceticus and TobM2 from S. tenebrarius on nebramine, were performed by supplementing 100 µM nebramine with the cell-free extract obtained from S. kanamyceticus (SK CFE) and TobM2 from S. tenebrarius (ST CFE). To minimize the presence of the kanamycin- or tobramycin-related congeners in the cell-free extracts of both wild-type strains, which might interfere with reactions, the cell-free extracts derived from glass-bead homogenization were further treated using OASIS MCX SPE pass-through as follows. At first, the cell-free extracts obtained from both wild-type strains were loaded onto each SPE cartridge, which was conditioned with methanol and water. Next, the pass-through from the cartridge was pooled, and the same step was repeated again. The above-mentioned cleanup procedures were all done in ice-cold conditions of about 4° C. The resulting cell-free extracts were incubated with compound 18 at 30° C. for 2 hours, and then subjected to the OASIS MCX SPE cleanup and HPLC-ESI-MS/MS analysis. Independent experiments were carried out in duplicate, and the results are shown in FIG. 8.

Reactions to determine the conversion of compound 6, 7, or 12 into compound 8 were performed by supplementing 100 µM of compound 6, 7, or 12 with the cell-free extracts obtained from S. kanamyceticus. These cell-free extracts derived from glass-bead homogenization were further purified using OASIS MCX SPE pass-through as described above. After incubation at 30° C. for 2 hours, the reaction was quenched. The resulting supernatant containing the product of interest was extracted using OASIS MCX SPE, and then subjected to HPLC-ESIMS/MS analysis. Independent experiments were carried out in duplicate, and the results are shown in FIG. 9.

EXAMPLE 10

Measurement of MIC of Kanamycin Biosynthetic Intermediates and Analogs

Minimum inhibitory concentrations (MICs) of various kanamycin-related pseudodi- and tri-saccharides and AHBA conjugated kanamycin analogs (except for compounds 16, 18, 19, and 20) were measured by broth microdilution according to the Clinical and Laboratory Standard Institute (CLSI, formerly NCCLS). As described in Example 2, gram-negative E. coli strains, P. aeruginosa strains, and clinically isolated strains were incubated in Mueller-Hinton broth (BD Science) at 30° C. Then, the aminoglycoside produced in the present invention was diluted 2-fold serially to give final concentration between 0.25 to 128 µg/ml. An aliquot of water was used as a negative control group. The growth of the strains was observed using the Labsystems Bioscreen C, and the minimum concentrations of the aminoglycoside diluted in the broth medium to inhibit the growth of the bacterial strains were measured.

EXAMPLE 11

3-Dimensional (3D) Implementation for Glycosyltransferases Such as KanF and NemD Homology modeling of a couple of glycosyltransferases such as KanF and NemD was performed with MODELLER and optimized by FoldX using the atomic co-ordinates of MshA (PDB code: 3C48) as a template. The 3D structure models were assessed by VADAR program. Molecular docking was employed to determine the binding conformation of the glycosyl donors (UDP-Glc and UDP-GlcNAc) and acceptor (2-DOS), and energy-minimized and structure-optimized with Gaussian03 using HF/6-31G(d) basis set for molecular dynamics simulation.

The docking of the glycosyl donors and 2-DOS to glycosyltransferases was initially conducted according to the predicted topological binding sites by several algorithms. The automated docking was carried out by CDOCKER program (Accelrys, Inc.) based on the MMFF force field and AutoDock 4.0 program suite. The active site was defined with 6 Å radius sphere from the putative catalytic center of KanF and NemD. Each complex model was solvated with TIP3 water molecules in a cube box and ensured the whole surface of KanF and NemD protein with their glycosyl donors/2-DOS to be covered by a water layer with a thickness more than 12 Å The energy minimization for each complex was performed using the steepest descent algorithm, followed by the conjugate gradient in the CHARMM. Then, a 500-ps position restrained molecular dynamics was performed with the proteins and glycosyl donors/2-DOS using CHARMM package. Finally, a 3 nanoseconds molecular dynamics was started by taking initial velocities from a Maxwellian distribution at 300 K. Solvent and glycosyl donors/2-DOS were independently, weakly coupled to a temperature bath with a relaxation time of 0.1-ps. The system was also isotropically, weakly coupled to a pressure bath at 1.0 atm with a relaxation time of 0.5 picoseconds and an isothermal compressibility of 0.5 $10^{-3}$/bar. Long-range electrostatics was calculated by the particle-mesh Ewald method. Short-range van der Waals and coulombic interactions were cut off at 0.1 Å. All bond lengths were constrained using the SHAKE algorithm, and the time step was set to 0.002 picoseconds. The binding free energies between the glycosyl donors and KanF (or NemD) were calculated using the linear interaction energy method using default parameters.

While the invention has been shown and described with reference to certain exemplary embodiments thereof, it will be understood by those skilled in the art that various changes in form and details may be made therein without departing from the spirit and scope of the invention as defined by the appended claims.

[Accession Nos.]
KABΔfn strain: KCTC11725BP
KABΔfnΔet$_2$a strain: KCTC11726BP
KCXb strain: KCTC11727BP
KABb strain: KCTC11728BP

INDUSTRIAL APPLICABILITY

According to the present invention, a kanamycin-producing Streptomyces species bacterium, a method of effectively producing kanamycin, and a new kanamycin compound produced by the same are provided.

The invention claimed is:

1. A vector for producing 1-N-AHBA-kanamycin comprising a gene set of
   kanA, kanB, kanK, kanF, kacA, kanE, kanC, kanD, btrG, btrH, btrI btrJ, btrK, btrO, and btrV.

2. The vector of claim 1, wherein the kanA, kanB, kanK, kanF, kacA, kanE, kanC, kanD, kanI, and kacL are derived from *Streptomyces kanamyceticus*, and wherein the btrG, btrH, btrI, btrJ, btrK, btrO, and btrV are derived from *Bacillus circulans*.

3. A *Streptomyces* species bacterium for producing 1-N-AHBA-kanamycin, expressing a gene set of kanA, kanB, kanK, kanF, kacA, kanE, kanC, kanD, btrG, btrH, btrI, btrJ, btrK, btrO, and btrV.

4. The *Streptomyces* species bacterium of claim 3, further expressing a kanamycin-resistant gene.

5. The *Streptomyces* species bacterium of claim 4, wherein the kanamycin-resistant gene comprises gtmF, gtmK, and gtmL derived from *Micromonospora echinospora*.

6. The *Streptomyces* species bacterium of claim 3, wherein the bacterium is *Streptomyces venezuelae*.

7. A *Streptomyces venezuelae* KCTC11727BP expressing a gene set of kanA, kanB, kanK, kanF, kacA, kanE, kanC, kanD, btrG, btrH, btrI, btrJ, btrK, btrO, and BtrV.

8. A method of producing a 1-N-AHBA-kanamycin using the bacterium of claim 3.

9. The method of claim 8, further comprising isolating 1-N-AHBA-kanamycin.

10. A method of producing a 1-N-AHBA-kanamycin using the bacterium of claim 7.

11. The method of claim 10, further comprising isolating 1-N-AHBA-kanamycin.

* * * * *

SEQUENCE LISTING

<160> NUMBER OF SEQ ID NOS: 62

<210> SEQ ID NO 1
<211> LENGTH: 825
<212> TYPE: DNA
<213> ORGANISM: Micromonospora echinospora

<400> SEQUENCE: 1

```
atgacgacat ctgcgcctga ggaccgtatc gaccaggtcg agcaggccat caccaagagc      60
cggcgctacc agacggtggc cccggccacc gtgcggcgcc tggcccgggc tgccctcgtc     120
gccgcgcggg gcgacgtgcc ggacgcggtg aagcgcacca agcgcgggct gcatgagatc     180
tacggggcct tcctgccgcc cagcccgccc aactacgcag cgttgctgcg gcagctcgac     240
tccgctgtgg acgccggtga cgacgaggcg gtccgggcgg ctctgcgccg cgcgatgtca     300
gtgcatgtgt ccactcgtga gcgattgccg cacctggcgg agttctacca ggagatcttc     360
cgtcacgtgc cccagcccaa cacgctgcgt gacctcgcct gtggcctcaa tccgctggcc     420
gctccctgga tgggcctgtc ggaccagacc gtctacgtcg cctccgacat cgacgcccgg     480
ctgatcggct tcgtggacgc cgccctgacg aggctgggcg tcgcgcaccg tacgagcgtg     540
gtcgacctcc tcgaggaccg ccttgacgag ccgaccgacg tcacgctatt gctgaagacg     600
ctgccctgtc tggagactca cgacgaggc tccggctggg aagtgattga cattgtcaac     660
tcgccgatta tcgtggtaac cttcccgacc aagtctctcg gtcagcgatc gaaggggatg     720
tttcagaact attcacaaag ttttgagtcc caggccagag aacggtcgtg ccgaattcag     780
cgactggaga tcggcaacga gctgatttac gtcattcaga aatag                     825
```

<210> SEQ ID NO 2
<211> LENGTH: 1407
<212> TYPE: DNA
<213> ORGANISM: Micromonospora echinospora

<400> SEQUENCE: 2

```
atgtctgaca cggccaaaca agcgaccggc gcggaggtca agcagcccgg cgcagcgggt      60
cccagccgac cgggactcgc gctgacccct ctggcctcct gtgcgttgat gatcgtcctc     120
gactcgacgg tggtctacgt cgccctgccg cagatccagc agagcctcga ggtgagcgcc     180
accgggctgg tctgggtggt caacgcgtac gccctggcgt tcggcggtct gatgctgctc     240
ggcggccggg ccggcgacat cgtcggccag cggcggatcc tcctcgtcgg gctggcggtc     300
ttcggcgtcg cctcgctgat ctgcggtctg gcgacctcgc cggagatgct gatcggtgcc     360
cgtgccctcc aggggatcgg ggccgcgctg gtcgccccga gtcgctctc gctgattccg     420
atcaacttca ccgacaacgc ggcccggaac aaggcgatcg gtgtctacac cggcatcgcc     480
gcggccggcg gcacgctcgg cctgatcctc ggcggggtgc tcagcgacgc cgcctcctgg     540
cgctgggtgt tcttcatcaa cgtgccggtg gtcgcgctgg tgctcctgct cgcgccgcgc     600
gtcctgcgcg agagccagcc gcagcgcggc tcgttcgaca tcgtcggggc ggtgacctcg     660
accggtgcga tggtcgccct ggtgtacgcg ctcgtccgca cctcgaccaa gggttgggc      720
gacccggtcg tcctggcctg cctcgccgtg gcggccgtcc tgttcaccgt gctgatcctg     780
gccgagcgtc gggcccggca gccgctgctg ccgctgcggc tgttcgccga ccgggtccgg     840
gccagcggct tcgtcaccct gctgttcttc ccggccgcct tcgccggcat gttcttcttc     900
ctcacccagt acttccaggg ggtgtggagc tactccgcgc tgcgtaccgg gttcgccttc     960
atcccggcgg cggtcctggt cctggtcgcc gcgatcctga gcggacagct ggtacccaag    1020
```

```
ctcggtccga gcgtcgtggc cgggatcggc gcgctgctca ccacgctcgg gatgatctgg   1080
ctcacccaga tctccgccga cggcggctac gtcacctcgc tgctcggtcc gctggcgatc   1140
gccggtttcg cgccggcct gatctactcg tcggtgaccg cctcgatcat gtccaacgtg   1200
gcgccggagg tgaccggcgc ggcgtccagc gtgttgcagg cggtccagca gatcggtccg   1260
gcgctgggac tggccgtgct ggtcaccgcg gcgggcacgc ccgccgaccc ggtcgagggg   1320
atgcgtaggg cgttctgggt ggctgccgtc atcgccgcgc tgccggccgt cctcgccctg   1380
ttcaaccgtc ggtcgcgtac cgagtga                                     1407
```

<210> SEQ ID NO 3
<211> LENGTH: 894
<212> TYPE: DNA
<213> ORGANISM: Micromonospora echinospora

<400> SEQUENCE: 3

```
gtgccggccg gtgaaccggc accggccacc cggccggagc cggagtcggc catcctgccg     60
gagccggccg cggccgtgcc gtcgccgccg ccggagtcac ccgccgtgca aaggtgatc    120 gcccggctca ccgccgcggc caagtaccgt gacgtgcacc cggagaccgt cgccgacctg    180
gtccggcggg agggtcgggc caccggggac gccgccgagc tggaacggcg ggtccgggcc    240
cggctgcaca aggtcgccgc cctgcacctg ctcaccgccc ggccggcggc gctgcgcaag    300
gcgctggacc gggccgacct cgacgacccg cagtcccggc gggactggtg ccggcaggtg    360
ctggccgggc acttctccac cgccgaacgc ctgcccgacc tggacaccct ctacccgacc    420
ctgttcgggc tggtgccgcc gccggagacg gtggccgaca tcgcgtgcgc gctgaacccg    480
ttcaccgtgc cctggctgcg ggaggtgagc gacgcccgct acgtcggcta cgacttcaac    540
gcgacgttcg tggagctggg caacgcgttc ctcgcccgga cccatccgga gtgcgagatc    600
cggcacgagg aggtgctcac cgacggccac cgggtgagcg ctgacctggg gttgctgctc    660
aagacgtacc actgcatgga gggacgccgg cccggcgccg ggctggcgct ggtcgaccgg    720
ctggcgtgcc ggcacgtggt ggtgtcgttc cccacccggg ccatgaacgg ccgggcggcg    780
gtcttcgtgc cccgtcacgt ggaggagctg gccgagctgg cccgcgaccg gggatggagc    840
tggtcgcggg ccactctggc gtccgaggac ctggtggcga tccacaagga gtga          894
```

<210> SEQ ID NO 4
<211> LENGTH: 1176
<212> TYPE: DNA
<213> ORGANISM: Micromonospora echinospora

<400> SEQUENCE: 4

```
gtgggcggta tgcaggtgca gatcctggcg ttgtcccgca gcctggccag ggcgggcgtc     60
gaccagctcg tgctgaccct gggctttccg gggttgccgc cgacgaagca gatcgagccg    120
ggcctgaccg ttcgtatcgc ccgggtgtcc ctgcccagaa tccgttccga gatcactgga    180
ttggtcggcc tgggacaggc atggttgatc ggaaccatcc gggagtgcct ccggttgcgt    240
cgcggtgact ggcgccccga tctcgtccac gtgcacgccg acggccagat ctggccactg    300
gtcgcgggtc ggatcgccgc ccggatcctg gcgtgccgt acgtgctcac cctgcactgc    360
tcccggctct ccgtctacca gccgatgtcg gcggtggacg cgatggcgca ccgcctggtc    420
acccaggcgg aacgacaggc gctgcgctcc gccgccgggg tcagcaccct gaccgccgc    480 accgccgacg tggtgagcgc cgcgaccggt ctggaccgct ctgccatcgt ggtcaacccg    540
```

```
gacgcggtcg acatcacccc ggccacgccc gccgaggcgg cggcgttcgc gcagcggtac    600
ggcctgaccg gccgccggcc gctcatcggc tacatcggcc gggtcgccca cgagaagggc    660
tggccggacc tgctccgcct ggccgaactt ctggacgacc tctccccgac cttcctcgtc    720
gtcggtgacg gccccagcg ggaacggatg gaacgggaga tcgccgaggc cggtcgcgcg     780
caccagttcg tggtgaccgg tttcctcccg cacgaccagg tgccggccgc tctcgcgctg    840
gtggacaccc tggtcatgcc ctcgatccac gaggaactcg ggcagcgc gatcgaggcg       900 atcatgacgg gcaccccggt cgccgcctac gcggtcgggg gactgcgcag caccatcggc    960
tcggcctgcc ccgacctgct cagcgagccc ggcgacgtac gcggactcgc cgacgtcgtc   1020
cggcacgtcc tgaccgaccg ggacgcggtg gtcgcgcaga tccacgccgc gcagaccagc   1080
accgccagca ccttcgacgt cgccgccacc cgggaccgga tgatcgactg ctaccgcgcc   1140
gccctcgccg gggccggggc ggcgagcggg aagtga                             1176

<210> SEQ ID NO 5
<211> LENGTH: 1173
<212> TYPE: DNA
<213> ORGANISM: Streptomyces kanamyceticus

<400> SEQUENCE: 5
atgcaggtca ccaccatcac gatggatgac gtccagtatc cctaccgatt aggcacggac     60
tgcctcgacg gcatcgtcac gcgcctcggc gaactcggcg ccagccgcta cctgatcgtc    120
agcgacccca gggtcgccga gctgtacggg caggggctgc gcaacggct cgcggagcag     180 gcgggacccg ccgagctgat cacccatgcc tcgggagaac agaacaaggg cctgcccgca    240
ctgcacgacc tggccgagga ggcgctgcgg cgcggcgccg accggcagag catcgtcgta    300
gcactcggcg gcggtgtcac cgggaacatc gcggggctgc tggccgcgct gctcttccgc    360
ggcatccgtc tggtgcacgt gcccaccacc gtggtggcca tgctggattc ggtgctctcg    420
ctcaagcagg ccgtgaacgc gggagtcggc aagaacctgg tcggcacctt ctaccagccc    480
gtcgaagtgc tcgccgacac cgcgatgctg cgcacccctgc cggtccgcga ggtcaggtcg    540
gggatgtgcg aggtggtgaa gaactcgctc gccatccgcc ccagcatgat cgaccagctg    600
tcggccgggc tgcgccccga cggccgctat ccgacgaca cgatgcactg gatcatctac    660
gagagcctgg ccgccaaggc ccaggtcacg gcgtacgaca gtacgagcg cggcgaggga    720 ctcatcctgg agtacgggca caccgtcggg cacgccgtgg agcactcctc gcagggagcc    780
gtgccgcacg gcgccgccgt cgcgctcggc atgatcgccg ccgcccaggt ctcccaccgg    840
gcgggctggg cctcggccga actcgtcgac ctgcaccggg agctcgtcgc caagaccggg    900
gtcgcgcggc gcatcccgtc cgacataccg ctctccgccg tcaggcaccg cctctccttc    960
gacaacaagc ggggctacct cccggcctcc gccgacacct atccgatggt gctgctcgaa   1020
tcccccggca aggtgctgcg cagcgagggc accgtcctga cggcggcgcc acgggacctg   1080
gtcgacgcgg tggtcgacga actcgcgaa ccccacggc ccgcggccgc gaggaccgac    1140
gacgccgcca ccgtcctcgg cggtgccggg tga                                 1173

<210> SEQ ID NO 6
<211> LENGTH: 1284
<212> TYPE: DNA
<213> ORGANISM: Streptomyces kanamyceticus

<400> SEQUENCE: 6
atgcccctgc aaagttcacg gcttgcggtc gacaacggaa ccccgtccg cggcaagccc      60
```

```
tggccggtgt ggccgcagcc caccgacggc accctcgacg ccctctcccg cgtcctgcgt    120
tccggccgct gggccatcag cggcccctac cggggcgtgg agtcggccga acgccgcttc    180
gcccgccggt tcgccgacta ccaccgcatc gcccactgcg tgcccgcctc cagcggtacg    240
gcgagcctga tgctggccct ggaggcctgt ggcgtcggcg cgggagacga ggtcatcctg    300
cccggcgtca cctgggtcgc ctccgcctcc acggtggtgg gcgtcaacgc ggtgccggtg    360
ttcgccgaca tcgaccccga caccctctgc ctcgacccgg acgccgtcga ggcggccatc    420
accccggcca ccaaggcgat cgtcgtcgtc cacctctacg cggccgtcgc cgacctcacc    480
cgcctcaagg aggtggccga ccggcacggc atcgtgctca tcgaggactg cgcgcaggcc    540
cacggcgccg agttcgaagg ccacaaggtc ggcaccttcg gcgcggtcgg caccttcagc    600
atgcagcaga gcaaggtcct gaccagcggc gagggcggcg ccgccatcac cgccgacccg    660
gtgctcgccc gccggatgga cacctgcgc gcggacggcc gctgctaccg cgatcaggcg    720
ccgccctccg gccacatgga gctcgtcgag acgggcgagc tgatgggcag caaccgctgc    780
atctccgagt tccaggcagc ggtcctgacc gagcagctgg gcgaactcga ccggttcaac    840
gccctgcgac ggcacaacgc ggaactcctc gacgcgctgc tgaccgacgt cggataccgc    900
ccgcagcgca gcacgcccgg caccaccgcc cgcacgtact acacctacgt cgccgagctg    960
cccgacgcgg aactgcccgg cgcggacatc accaaggtca ccgaggcgct gaccgccgaa   1020
ctcggcttcc cggtggcacc ggcctactcg ccgctcaacg ccaaccccct gtacgacccg   1080
gccagtcgca gccggttcgc cctcggaccg cagcacgaga gctcatcga ccccgcccga    1140 ttcgtgctcc cggtgagcgg ccgcctgacg cgtcggctcg tcaccttcca ccacgccgcc   1200
ctgctcggcg acgagtcgga catgagggac atcgcggaag cgttcaccaa ggtgctccag   1260
caccgggccg tcctggccgc ttga                                           1284

<210> SEQ ID NO 7
<211> LENGTH: 2064
<212> TYPE: DNA
<213> ORGANISM: Streptomyces kanamyceticus

<400> SEQUENCE: 7
gtgaaggcac tcgtgttcca cagccccgag aaggcgacct tcgaacagcg cgacgtcccc     60
actccccggc cgggcgaagc cctcgtccac atcgcgtaca actccatctg cggcagcgac    120
ctctcgctct accgcggtgt ctggcacggc ttcggctacc ccgtcgtgcc cggacacgag    180
tggagcggca ccgtggtcga gatcaacggc gccaacggac acgaccagtc gctggtcggc    240
aagaacgtgg tgggcgatct gacctgcgcg tgcgggaact gcgcggcctg cgggcgcggg    300
accccggtgc tctgcgagaa cctccaggaa ctcggcttca ccaaggacgg cgcctgcgcc    360
gagtacatga ccatcccggt cgacaacctc cgcccgctgc cggacgcgct gtcgctgcgt    420
agcgcctgcc aggtcgaacc gctcgcgtg gcgctcaacg cggtcagcat cgcgggcgtc    480
gctcccggtg accgggtcgc cgtcatgggg gccggggca tcggcctcat gctgatgcag     540
gtcgcgaggc atctcggcgg tgaggtgacg gtcgtgtccg aaccggtcgc gaacggtga    600 aggcactcgt gttccacagc cccgagaagg cgaccttcga acagcgcgac gtccccactc    660
cccggccggg cgaagccctc gtccacatcg cgtacaactc catctgcggc agcgacctct   720
cgctctaccg cggtgtctgg cacggcttcg gctaccccgt cgtgcccgga cacgagtgga   780
gcggcaccgt ggtcgagatc aacggcgcca acggacacga ccagtcgctg gtcggcaaga   840
```

```
acgtggtggg cgatctgacc tgcgcgtgcg ggaactgcgc ggcctgcggg cgcgggaccc    900
cggtgctctg cgagaacctc caggaactcg gcttcaccaa ggacggcgcc tgcgccgagt    960
acatgaccat cccggtcgac aacctccgcc cgctgccgga cgcgctgtcg ctgcgtagcg   1020
cctgccaggt cgaaccgctc gcggtggcgc tcaacgcggt cagcatcgcg ggcgtcgctc   1080
ccggtgaccg ggtcgccgtc atgggggccg ggggcatcgg cctcatgctg atgcaggtcg   1140
cgaggcatct cggcggtgag gtgacggtcg tgtccgaacc ggtcgccgaa cggcgcgcgg   1200
tcgccgggca gttgggcgcc accgagctgt gctccgccga gccggggcag ctggccgaac   1260
tcgtcgcccg cgcccccgag ctcacgcccc acgtggtcct ggaggcatcc ggctatccgg   1320
ctgcgctcca ggaggccatc gaggtggtca ggccgggcgg ccgcatcggc ctgatcggct   1380
accgggtgga ggagacggga ccgatgtccc cgcagcacat cgcggtcaag cgctgacccc   1440
tgcgcggctc gctgggcccc ggcggccgct tcgacgacgc cgtcgaactg ctcgcgaagg   1500
gcgacgacat cgcggtcgag ccgctgctca gccacgagtt cggcctcgcc gactacgcca   1560
ccgcgctcga cctggcgctg tcccgcacga acggcaacgt gcgctccttc ttcaacctgc   1620
gcgactaggc gcgcggtcgc cgggcagttg ggcgccaccg agctgtgctc gccgagccg    1680
gggcagctgg ccgaactcgt cgcccggcgc cccgagctca cgcccgacgt ggtcctggag   1740
gcatccggct atccggctgc gctccaggag gccatcgagg tggtcaggcc gggcggccgc   1800
atcggcctga tcggctaccg ggtggaggag acggaccga tgtccccgca gcacatcgcg   1860
gtcaaggcgc tgaccctgcg cggctcgctg ggccccggcg gccgcttcga cgacgccgtc   1920
gaactgctcg cgaagggcga cgacatcgcg gtcgagccgc tgctcagcca cgagttcggc   1980
ctcgccgact acgccaccgc gctcgacctg gcgctgtccc gcacgaacgg caacgtgcgc   2040
tccttcttca acctgcgcga ctag                                         2064
```

<210> SEQ ID NO 8
<211> LENGTH: 1164
<212> TYPE: DNA
<213> ORGANISM: Streptomyces kanamyceticus

<400> SEQUENCE: 8

```
atgcaggtac agatcctgcg gatgtcccgc gccctggccg agttgggggt gcgccagcag     60
gtgctcaccg tcggcttccc cggtctgccc agagtgcggc gcgactccga gaacctggtg    120
gtgcggatca ccagggcccc gctgcccagg ctgcgctcca ggatcaccgg cctggtcggc    180
ctcaaccagg cgtggctggc cgccgcgctc accgaatgcg tgaaactgcg gcgccgctgg    240
cccgccgacc tgatccaggt ccatctggac ggccagctct gggcgttgct cgcgggaccg    300
gtcgccgccc gctggtggg cgtgccgtac acggtcaccg tgcactgctc gcggctggcg    360
gtgtatcagc ccatgtccac cgtcgaccgc atccagcacc ccttggtgac cgccgtcgag    420
cgctgggcgc tgcgccgtgc ggccgggatc accacgctga ccgagcggac cgccacggtg    480
ctcgccgccg aactgggcgc ggcccagagg gtgatcgacg tggtgcccga cgcggtcgac    540
cccgatcggg ccgaggccgc gcccgccgag gtcgagcggc tgaagaagcg tttcggcctg    600
ccgcaggagg gcggtcccgt catcggattc gtcggccgga tcgcccacga aagggctgg    660
cgccacgccg tccaggcggt ggccgaactc gcggacgcgg gccgggactt caccttcctc    720
gtcgtcggag acggaccgca gcgggccgac atggaggcgg cggtggccga ggccggtctc    780
accgaccggt tcgtcttcac cgggttcctg cccaacgacg agatccccgc cgtgatgacc    840
gccctggacg tcctcctgat gccgtccgtg cacgaggagt tgggcggcag cgccgtcgag    900
```

```
gccatgctcg cgggaacgcc ggtggccgcc tacggggtcg gcggcctgtg cgacaccgtg    960
ggcaaggtga ccccgtcctt gctggccgcg cccggccagg tggccgaact cgcgcggacg   1020
gtcaagcggg tactcgacga tcccgcgccg gtcctggccg aattgcgtgc cggacgggag   1080
tggctcgcgg acgagttcgg tgtccaccac gcggccggtc tcgcgttggc ccactatgag   1140
cgggtactcg gcaaagaacg gtag                                         1164
```

<210> SEQ ID NO 9
<211> LENGTH: 750
<212> TYPE: DNA
<213> ORGANISM: Streptomyces kanamyceticus

<400> SEQUENCE: 9

```
gtgagggtcc tcctcgtctc ccccaccccc gacgacatcg cgctgtcctt cggcggctgg     60
gtcgcggccc acgcccgcgg gctcgcggcc aagggctggc ggttcgacct gctgaccgtc    120
ttcggcacga ccctgtacgc gccccacagc ccgcgcgccg tcaccaagga ggccatcagc    180
acgctccggg agcgcgagga ccgcgactac gcgcgccgtc acgggctgcg gctgacctct    240
ctccggcagg aggactgctc ctgcctgggc atggacgacg aggaggagct catcgccccc    300
gaggcgaccg atcctcgccg gccgccgtg cggcagctga tcgcggcggc gctcgccggg    360
gccgacctgg tcgtcgcgcc gctggctgtc ggcggccacg tggatcaccg catcgtccgc    420
accgcggtgc ggcagtcgct cggcgccacc ccctgcctct ggtacgagga cctgccgtac    480
gcgttggaga gccccgtcga ggtgccctcc gaccaccggc cctggctggt cgacatcagg    540
gggcacgagg cggccaagcg cgccgatctc gcgctgtacc gctcgcagat gaccgccgcc    600
gacacctccg aggtcctctc gtaccggccg gacggcgcgt ccgtcccgtg cgagcggctc    660
tggagttcgg cgggcttccc ccaggacctg gccgagcgga tggcactggc cacgctggcc    720
gccgtgacac ccgacaagga gtcgctatga                                   750
```

<210> SEQ ID NO 10
<211> LENGTH: 1170
<212> TYPE: DNA
<213> ORGANISM: Streptomyces kanamyceticus

<400> SEQUENCE: 10

```
atgggcggca tgcacctgct ggtgcgggcc ctggtcgagg agatggcggg ccgcggcgtc     60
ccgcaccggg tcctgacgat gtcaccgccc aaggtgccca aggacatcag gatcgggcag    120
cggatcaagg tgcacgcccg gcggctgccc gtgctgccca tcccctccga cctggagggg    180
tacttcggac tcgtcggcgc ctgggccaag ggcagcctgt tgtgggtgct gcgcaaccgc    240
aagcggctgc gccgggagat cggggcgcgg gtgcacgcgc actgcgacgg ctcgggcgcc    300
gcggccttct acccgtatct gatgtcccgg atcctcggcg tgccgctggt ggtccagatc    360
cactccagcc gctatctgag ccagcacccc accacgctct cgagcgggt gaccgacccg    420 atcgccaagt gggcggagcg gcacgccgtc cgcaaggccg ccgcggtcct gatgctcacc    480
gaccgggccc gcgacgagat gcggcgcaag gcccagctgc ccgcggagcg cgtgcaccgg    540
ctcgcgtacc tggccagcga ccagttcaag gacgccgaca ccgaggcgag gcgggcggaa    600
ctgcgggagc gctacggcct cgacgaccgc ccgatcgtgc tctacgtggg gcggatcgcc    660
gccgagaagg gcgtggagta ctacatcgag gccgcggccg aactgacccg caggggccgg    720
gactgccagt tcgtcatcgc cggggacggt cccgcccggc cggacctcga aaagctgatc    780
```

| | |
|---|---|
| ggcgcccgcg ggctgcgcga ccgggtgacc atcacgggct tcatgtccca cgagttcatc | 840 |
| ccatccatga tctccctggg cgaactcgtg gtgctgccgt cccggtacga ggagctgggc | 900 |
| atcgtcatcc tggagtgcat gaccatgcgc aggccgctgg tcgcgcacga cgtgaacggc | 960 |
| gtcaacaagc tcatcgagga cggcaccacc ggaatcgtcg tacccccgtt caggaccccg | 1020 |
| gagatggccg acgccgtcga gcggctcctc gacgatccgg agctgcgcga gcggatggcg | 1080 |
| gagaacgccg ccccgctgcc cgccgccaag tactcgctct ccgcggcggg cgaccaactg | 1140 |
| gcgggcatct accgggagat cgggctgtga | 1170 |

<210> SEQ ID NO 11
<211> LENGTH: 1080
<212> TYPE: DNA
<213> ORGANISM: Streptomyces kanamyceticus

<400> SEQUENCE: 11

| | |
|---|---|
| atgggcgggg tgcacgccga ggtggtggcg gctcatcccg cgcccggct cgaagcggtg | 60 |
| cacgacctcg accccgccgc cgccaggac ctggccgagc ggttccgcgc cgagcgggcc | 120 |
| gagccctcct gggcggacct gctcgccgac cccgcgatcg acctgctcat catcaccacg | 180 |
| cccaacgggc tgcaccaccg gcaggcgcc gaggcgctgc gggcgggcaa gcacgtactg | 240 |
| gtggagaagc cgctcggtgt cacgccggag caggtggccg agctcgtcga actcgccgga | 300 |
| cggcacgacc gggtccttgc ccacggaagc aacttcgtgc acagcccgaa gttcgtccgg | 360 |
| gcccgtcaac tggtcgcgga caccgaggcg ttcgacggc cgcacctggt ccgggtcgtc | 420 |
| ttccgcaact cgggccccga ggccgcctgg gccgcgtcca aggacctcgc gggcggcgga | 480 |
| gccctcctgg acctgggctg tcacgcggtg gagctgtgcc ggtggctgct cgacggcgcc | 540 |
| gacgtcgagt cggtcagcgc ccgactgcag cgggtgcggc cgcccacga cgccgaagcg | 600 |
| gaccgcgcgt ccggcaccgc gggaaccgcg cgggtcgcgc tggaggacca ggcgctgctg | 660 |
| gtcatggagt tcgccgacgg cgcggtcggg cagtgcgacg tctcctgggt cacccagggc | 720 |
| ggtgagcagg tcaccgcgga gatcatcggc accaagggca gggtcgaggt cgacctgtgg | 780 |
| accggcatgg ggctgcgcgc ctactcggac aagggctatc aggacgtctg ggatcccgag | 840 |
| cagggctggg tgcatccgga atgggagtgg atccgggcga gcggctacta ccaccaggac | 900 |
| ggcaccgtga tcgaggcggt gggccagggc atccccctca cccacggccc cgcggaagcg | 960 |
| ctcgcctcgg cccgtgtcct ggccaccggt taccgcagtc acgcggaggg cgggtactg | 1020 |
| cggctgtccg gcgcgccggt cggccctggc gcgtcgacga cggcggcggg ctcggaatga | 1080 |

<210> SEQ ID NO 12
<211> LENGTH: 1260
<212> TYPE: DNA
<213> ORGANISM: Streptomyces kanamyceticus

<400> SEQUENCE: 12

| | |
|---|---|
| atgagcaaga agctggcgct gttcggcgga actcccgtac ggaacgagga gttctacgac | 60 |
| ggcccgcaca tcgggccgca cgatctcgac cgcctcaaat ccgtcctcga ctcggggaac | 120 |
| ttcggcggca tccccttccc caacacccac acaccgcct tcgccgacct gttcaccggc | 180 |
| aagctcggcg ccccgtacgg cctgatggtc tccaacggca ccatcagtct ctccatcgcg | 240 |
| ctgcgcgccc tgggcgtgcg tgccggggac gaggtgatca ccaccggcta cacctggatg | 300 |
| ggcacggccg cggcgatcgt gcacatcaac gccgtccccg tcctggtgga catcgacccc | 360 |
| acgacctggt gcatcgaccc ggcggcggtg gaggcggcga tcaccccgcg caccaaggtg | 420 |

```
atcgtcccgg tccatctggg caatcagatc gccgacctcg acgcgctgcg ggcgatcgcc    480
gacaagcacg gactcgcgat cctggaggac accgcgcacg ggcacttcgc cgagtggcgg    540
gggcagtgcg tgggcaccca cggggacgcg ggcagcttca gcttcgagag cagcaagatc    600
atgactgccg gtgagggcgg cttcctggtg gccaggacg aggacgtgta ccagcggatg      660
atgtcgctgg ccaactgcgg ccgcaaggag ccgggttacg acggtttcgc gggccgcacc    720
ctgggctgga acgccgcgc gagcgaactg caggccgcct tcatgatcgg gcaggtcgag      780
cagcacgacg cgctgcacgc caagcgggcg gcgagcgcgg cgaagctcac cgcggggctc    840
gccgagatcg gcggcttcac tcccgtgggg aacgacgacc cgaggatcac ccggcgccag    900
tactacgagg tcatctaccg cttcgacccc gccgctgggg aggggctgca ccgggacgag    960
gtcctctcgg cgatccttgc cgagggcatc gagctggagg gcgacgcctt ctacccgccc   1020
gtacacaaga gcgaactgtt cgcggtggac gccgtccact ggcccatgat cgccgagagg   1080
tacggcgatc ggatcggccc ggacagcgtc gacctgcccg tcgccgaccg cgccgccgcc   1140
gacgagtccg tgtgggtgca ccacgcgctg ctcaccggcg acgacaagga cctcggcgac   1200
atcctcgaag ccgtcgccaa ggtccgcgac aacctgcgag aactgcacga cgcgagctga   1260
```

<210> SEQ ID NO 13
<211> LENGTH: 1527
<212> TYPE: DNA
<213> ORGANISM: Streptomyces kanamyceticus

<400> SEQUENCE: 13

```
gtgcgcatca tctccgtaca ggaggcggcc acccgcacct tcgacgtctg cgtggtgggc     60
agcggcgcct ccggtgccat caccgccgcg gtgctcgccg aacggggcct gtccgtgctc    120
atcctcgaac agggcaccgc gatcccgccg ggcaccgacc acgacgacgt cgaggacccc    180
gacacctggg cgtacgcacg cgacggggaa ggctggagca aggagggcta tccctggagc    240
gccatggcgt tcggcggcgg cacggtgttc tacggcggca tctccttccg ctacgaacag    300
cgcgacctcg acccgccgcc cgcgctcctc ggcgacgccg actacgcgca ctggcggctg    360
cggctcgacg aactggagcc gcactacgac tgggtggagg accggctcgg cgtgagcggc    420
ccgtcccacg gccgggtggg cgactacgcc ttccccact acgcgcgggg ctcgctgccg     480
cacacccega tgggcggcgc gctggcccgg ggcgccgacg ccctgggget gaccccgctg    540
tccaccccga tggcgatcag cggggccagg gaccggcacg gccccggctg cgccgagctg    600
acgccgtgca ccggcttcac ctgccccggtc aacgccaagg ccgatgtgat cagccgcatc    660
ctggcgcgcg ccgaggggga cgtgtccgtc gccctggaca ccagagcggt gcggttcgtg    720
gcctcggcac cggggcggc gaaacgtctc gaagtgctcg gcggcagtcc ccgcagccgc    780
cgctcggtcc atgccgaccg cttcgtcctc gcggccaacg ccatccagtc cgccgcgctc    840
ctgctgcgtt cggcggaccg gcgcgagccg acggcatgg ggaactccag cggtcaggtg      900
ggccgccacc tggccatgaa gaacagcgtc tacgtccgcg gcaggaccca ggagcggatc     960
gtcgcccacc agccgctgcg ccatcgctac tccagcgtct gcgtcctgga ccacctgcgc   1020
ggtgcggagt tccccgggca gctgggcggg atcatctacg aggccaaccc gtgggaggac   1080
cccgaggccg accgtcctgg cgccggttcg ctgctccagc tggagtgcct cctcggcgac   1140
cgcccgcagg cccgcaacat ggtgcggctc gccaggagcc gggaccggga cgggctccag   1200
cgcatcgtca tggactaccg ccagcacccc ttggacggcg aacgcctgga cgtgctccag   1260
```

```
gggaaggcga aggatgtact gcacgcggcc ggggccgagc gcaccgagtc cgtcgacagc    1320
gatttcgcga ccggcagcac gcatctgcac ggcacgctgc gcgccggtga cgaccccgcg    1380
acctcggtga ccgaccggac gggccggctg cacgactacg acaacgtgtg gtcggcggac    1440
ggcgcgacgt tccccttcgc cgggaacttc aatcccaccc tcaccatcca ggccaatgcc    1500
cggcggatcg cggtcggcat ctcctga                                        1527

<210> SEQ ID NO 14
<211> LENGTH: 1179
<212> TYPE: DNA
<213> ORGANISM: Streptomyces kanamyceticus

<400> SEQUENCE: 14
gtgtccacgc accccgtcct ggactggagc cgatccgccg aacacctgcg ccgctcccac      60
ggcgtcacca ccgaccccccg ccccgacgag gacggccact accctgcgt actgacccgg    120 ggcagcggca ctcgcgtgta cgacctggac ggcaacgcct acctcgatct caccggatcc    180
ttcggctcgg tgctcatcgg gcacgcggaa ccggccgtcg tacgggcggt gaccgacgtc    240
ctgagcgaag gcaatctctt ctacaccggc gcgagcccgc gccgactggc cctcgcggag    300
cggctccttg actggttccc ctggtccgag caggccatct tctaccgcac ggggtcctgc    360
gcggtgtccg cggcggcccg gctcgcccag cacgcgaccg gccgcaaccg ggtgctgagt    420
tccggctacc acggctggca cgactggcac ctggaggcgg tgcccgaggc caagcccaag    480
accttcgagt cgtacgccac cgagttccac aacgacctgg cgctctaccg ctcctggctc    540
gaccggcacg gcgaggagat cgcggcggtc gtggtgacgc ccgagccgca ccgcttcgac    600
cacgcctact accaggagct gcgcgaggtg gccaaggagc acggctgcct gttcgtcgtg    660
gacgaggtca agaccggctt ccggggccggg gcggggcggt tcagcgccct ggccgggatc    720
gagccggacg ccgtgaccgt ctccaagggc atggccaacg acacagcat ctccgccgtg    780 gtgggccagc gacagctcac ccaggagctg agcgaggcg acgtctggtc cacctaccag    840
aacgaacagg tggggttcgc cgccgcgttg gcgtccctgg acttcctgga gcggcacgac    900
gtggcggccg tgacgcgccg cacgggtgag gcggtccggc agggcgtgct ccagctcttc    960
gccgaacacg gcctgcccgt cggggcgccg ggctggggac cgatgttcga gctggacttc   1020
gacgccgccg acgagggtct cgccgagcgg ctcgaagcgg cgctgctgcg ccacgggatc   1080
ttctgcgaca cgggcgacga cttcaacatg atgttccata ccgcggagca caccgacgag   1140
ctcctcgagc ggttcgccgc cgcgctcggc gacctctga                          1179

<210> SEQ ID NO 15
<211> LENGTH: 783
<212> TYPE: DNA
<213> ORGANISM: Streptomyces tenebrarius

<400> SEQUENCE: 15
atggagcaac ggtacgtgct ggtcaccggg gccagtcgcg gtctgggacg gcgcagcgcc     60
gaggagctgg ccggccgagg gtggaccgtc gtcctggcct gccgcgacgt cgcggacgtc    120
gcgtcactgc tcgcgacggt gcgcggccgg ggcgccaggg cccacgcggt tccgatggac    180
gtgaccgacc cggacagcgt cgccgcgcg gtggacgccg tgcgcgaggt cggcgggcgg    240
ctgcacgccc tggtgaacaa cgccggggtg ttccgtcacg ccgaggagcg cttcccgggg    300
ctgacgccgg gggacgcgct cgacatcctg ctcaccaaca cctacggccc gctggtggtg    360
accagggcgt tcctccccct gttgcgcgcc gcggggcgggg cggcggtggt gaacgtgacc    420
```

-continued

```
agccgcgacg ccgacgagga caccttcgac ggcgagttca cctgctaccg cgcgtccaag    480
gccgcgctga acgcgatgac caggaacctg cggtcgcgc tgcgccccga ccggatcgtc     540
gtcaacgcgg tcgatccggg gtggatcccc accgacatgg gcggtccgga ggccccggac    600
agcctggacg cggccgtgac ggcggtggtc gacgccgtcg agctggccgg gagcgaccgg    660
accggggtcc tgctcagggc tggccgcgac cccgcccctc cggtggcggc gccgagcgag    720
cccaaccagc ggcaccagcc ggacctcccg ccgccccccg tcccgcggtg gtcggcgtcg    780
tga                                                                   783
```

<210> SEQ ID NO 16
<211> LENGTH: 1383
<212> TYPE: DNA
<213> ORGANISM: Streptomyces tenebrarius

<400> SEQUENCE: 16

```
gtgaatgagg tgcgacgaat gcggctcggc acggtactgc tggtgagccc gaagacttcg     60
ttcgggcgtg atctgcaacg gacgtacgcg ggcgggctcg gcacggtctg caaggacgag    120
gacttcctgc tgcccccgct cgacctgatg cgcctggccg cgtcctgcg cgaggacgcc     180
gacgacatcg cgatcgccga cgaggaggtc accggcgtgg tcccctccgt ggagcccggc    240
accacggtga tctgccacgt ctcgctgccc agcctgctgg aggacgccga gcggctggcg    300
accttccgcg cgcagggcgc ccgctgctac gcctacacga gcatccgcag ccccgcccag    360
tggcggaccc tgttcgagcg gggcggctgc gagggcgtcc tgctccccga gtcgatctcc    420
ttcgcccgcg ccgcgctcgc cggcgaccac accgtgccgg gcctggtgac cccggactcg    480
ctgctcgacc cccggcacca ccagccggcc ttcggtgacc tggcggccga gccgctgccg    540
gccagggacc tggtcgacca cacgccgtac atgttccccc cgatcgcgcg caccgggatc    600
accagcatca acggcagctt cggctgcccc tacccgtgcc gcttctactg cccgtacccg    660
ctcagcgagg gccgcaagat ccgcacctac cccgtcgagc ggatcgtggc ggagttccgg    720
cagtgcgccg agctgggcat caccgcggcc gtcttccgcg acccggtgtt ctccttccac    780
cgcgaccgca ccctggagct gtgccaggcc ctcaaggccg ccgacaccgg ggtgccctgg    840
tggtgcgaga cccggatcga ccggctcgac gaggaggtcg tggccgcgct ggtcgacgcc    900
gggtgcgtcg gcgtcgaggt cggcgtggag agcggcgacc ccgacatgca ggcgaccgcc    960
gtccgcaagc gcctgaacct ggacaccgtc cggaagttcc acgcggtggc caggaaggcc   1020
gggctgaagc tggtcttcct gttcctgatc ggcctgccca gggagaccag gatgtcgatc   1080
cggcgcacct tcgacttcat cctggagctg gggctggccg acaccgagtt caacctcagc   1140
gtgatcaccc cctacccggg caccgagctg caccagatcg cggtggacaa ggggtggatc   1200
gacggctcgc agaacgcctt caccagccac aacgccgtga tgcacaccga cgagctgagc   1260
atcggcgacc tggagcgggc cagccggttc gtcgacgagc tgcacgcggt ctgcaaggcg   1320
gggcccgccg agcgggccga gttccaggcc agggtgcacg cctggtcgac cggtgacgcc   1380
tga                                                                 1383
```

<210> SEQ ID NO 17
<211> LENGTH: 1251
<212> TYPE: DNA
<213> ORGANISM: Streptomyces tenebrarius

<400> SEQUENCE: 17

-continued

```
gtgcgtgttc tccggctcac cccgttcttc caccacgact gcgtcacctc gtggccggcc      60
gagttcgacg cggtcggcgg gatgcagttg cagatcctgc ggctgtcccg cgagctggcc     120
cggcgcggcg tgcgccagca ggtgctcacg ctgggcttcc ccggcctgcc ccgggtgcgg     180
gtcgactcgc cgaacctggt cgtgcggatc accagggccc cgctgccccg gctgcggtcg     240
gagctgaccg gcctggtcgg gctcaaccag gcgtggctgg tcgccgcgct ggccgcgtgc     300
gtgcggctca ggcgcacctg gcgccccgac ctggtccacg tgcacgccga cggccagctc     360
tgggcgttgc tggcgggacc ggccgcgtcc cgcgtgctcg gcgtgcccta ctgcgtgacg     420
ctgcactgct cgcgcctgtc ggtgtaccag cccatgtcgt ggatcgacca gctccagcac     480
cggctggtcg tcgcggcgga gaagtgggcg ctgcgcgggg cctccggcgt gtcgaccctg     540
accgaccgca ccgcgtcggt ggtcgcctcc gcgctcgggg tgggcgcgga ggacgtcgac     600
gtggtccccg actcggtgga cacgtcgtcc actgtggaca gagcagaggg gcgcgtgctg     660
ctggagaagc tgggcgtgcc gtccgaccac gaggccgtcg gctacgtcgg ccgcgtcgcg     720
cacgagaagg gctggcccga cctcgtgcgc gtggccggcc cgctgtccga ccggaaggcg     780
accttcctgg tcgtcgggga cgggccgcag agcgggcgca tgcgcgacga ggtcgccgcc     840
gccggcctgt ccgaccggtt cctgttcacc gggttcctgc cccatcacga catcccggcg     900
gtcatggccg gtctggacgt gctcgtgatg ccgtcgcggc acgaggagct gggcgggagc     960
gcgctggagg cgatgctggc gggaacgccc gtggccgcct acgccgtggg tgggctgcgg    1020
gacaccgtgg gccacgtgac gccgtcgctg ctcgtgcctc ccggcgacgt cacggcgctc    1080
gcggaggccg ttcgtggtgt gctcgacgac ccgcggcccc accgcgacca ggtggccggc    1140
ggccgttcct ggctgaccga cctcttcgac ggcggtgccg ccgcgcgtcg ggtgatcgcc    1200
cactatgagc gtgtcctcag tggaaccgcc cgtctccgcc ctcaggaata g             1251
```

<210> SEQ ID NO 18
<211> LENGTH: 1263
<212> TYPE: DNA
<213> ORGANISM: Streptomyces tenebrarius

<400> SEQUENCE: 18

```
gtgcggcggc ggggcggcgt gctggcgctc accccgttct tcctctaccc cgagtaccag      60
gactgctggt cggcccggtt cgactcgatg ggcgggatgc acctgctggt gcgggcgctc     120
gtggaggaga tggccggcag gggcgtcccg caccgcgtgc tcaccatggc cccgcccggc     180
gtgcccaggg acctggccat cgcccgcaac gtcaccgtcc acgcgcgacg cctcccggtg     240
ttgccgatcc cgtcccagtt ggaggggtac ttcgggctgg tcggggcgtg ggccaagggg     300
agcctgctgt gggtcctgcg gaaccggagg cggctgcggc gggagatctc cctggtgcac     360
gcccactgcg acgggtcggg ctcggcgccg ttctacggct ggctcatcgc gcgggcgctg     420
ggcgtgccgc tggtggcgca gatccactcc agccggttcc tgagccagca ccccacgacg     480
ttgtgggaac gggtcaccga cccggccgcg aagtgggcgc agcggttcac cgtccgcaac     540
gcggcggcgg tgctgatgct caccgagaag gcccgcaccg agatgcggga cgcggcggcg     600
ctggaccccc ggcgcgtcca ccggctgccc tacctggcca cgaccgcctt cgccgagggc     660
gacaccgagg agcggaggac cgagatcagg cggcgcttcg gcctggacac cggccagccc     720
gtcgtcctct acgtcgggcg gatcgcggcc gagaagggcg tggagttctt cgtcgaggcc     780
gccgccgaac tgcggcggcg cgggcgtaac tgccggttcc tcgtcgcggg ggacggcccg    840
acccgccagg agatcgagaa gctggccgag gacaggggcg tcgccgaccg gatcacgatc     900
```

```
accggtttcc tgccgcacga gctgatcccc tcggtgatgg cattgtccca gctcgtggtc      960
ctgccctccc ggtacgagga actgggcatc gtgatcctgg agtgcatgag catgcgccgg     1020
ccgatcgtcg cgcacgacgt caacggcgtg cacaagctca tcgagcatgg caggaccggg     1080
ctgttggtgc cgccgttcga cacgcccgcg atggccgacg ccatcgaggc gctgctggac     1140
gacccggagc tgcgggagcg gatcgccgag accgccgccc gctgccgtc cgcgaagtac      1200 tcgctgacca cggcggcgga ccagctcacg gacatctacc gggagctggg cgtatgcgtc     1260
tga                                                                   1263
```

<210> SEQ ID NO 19
<211> LENGTH: 471
<212> TYPE: DNA
<213> ORGANISM: Bacillus circulans

<400> SEQUENCE: 19

```
atgattagct ggacgaaagc ttttaccaag ccgttaaagg ggagaatttt catgcccaac       60
ttatttgtct acgggactct gcgtgaggga gaaaacaacc acaagtatat gaagaagcc       120 accctgcttt cgcgaaaggc cagcatagcc ggttccttgg tagataccgg caacggttac      180
cccggcttac tgctggaaaa tcagctggtg gcgggcgagt ggtatgaagt ctcggaagaa      240
acgctgaaac ggatagatga gctggaagag tatttcggtc ccggggatac aagaaactta      300
tttgacagaa tcgaatgcca agtaaacgag agcggcggaa cacatctggg ttggacgtac      360
gtgtacaacc gggacgatta cctggaaaca aggttttccg actggaaaca ataccggctg      420
cagcatgctt ccggaataga ggagaagcaa gatgtgcctc actcgttatg a               471
```

<210> SEQ ID NO 20
<211> LENGTH: 909
<212> TYPE: DNA
<213> ORGANISM: Bacillus circulans

<400> SEQUENCE: 20

```
atgtgcctca ctcgttatga cgagaaattt ttcgattgca gaaaatcgca gataatcgct       60
tatttggact cacaacaggt ccccgtcatt cctctatttt ataacagtta tcaaagcaca      120
gcggaaattt accgccagat ctttatcgaa aataagagca aatggaagta ttcagagcct      180 tcttttccg acgatgattt actaagaaaa ggaattaggc ctgttcgggc ttcttttccc       240
gacttcagcc aggcttcgga ttgtttaaag gatctgctgg cccggcataa actcgttttc      300
gtatgggggg acgagtattg tctgccttac cggaaggaag ccttccaggc cattcattcc      360
actcattcgc ttgttgtcac gggctatgac ggtgagaaca aggcatacta cgtggaagat      420
tgggacgggc tctacggata tttgccggct gtacatttgg aagcggcttt cgacagtctg      480
tccaggcaga tgaggacatt gttggttctg aactgaacg acgaggaaat gcgggaaaac      540
aaacaagagg atacagattt gttccggaag tggctgcaag ccttcgagga cgactatatc      600
ttctacgacc gggtgctgct ggatatgcgc gattatgagg aaaaccggct gatctcgatg      660
gatcacggac ttcgtttaat cgccgcatcc cggcatgttt tctccaagtt tcttcattat      720
atagatgacg ccccggagga ggtcggcctc cttatccgca accatcaact cgctaaccat      780
atcgcggcca tcgtcaggcg gtacattatc gccaaacaga ttgattggga cggggcagct      840
tgcaagattc ggcaattaag agagcaagag gatgacttta gcggaagct aaagagccgt      900 tacggctaa                                                              909
```

<210> SEQ ID NO 21
<211> LENGTH: 264
<212> TYPE: DNA
<213> ORGANISM: Bacillus circulans

<400> SEQUENCE: 21

| | | | | | |
|---|---|---|---|---|---|
| atgtctttag | aaactcagga | aaatgttcgg | accgctcaaa | ttgtatcttg | cgtgaatgaa | 60 |
| attctgcaga | cgaaggaatt | cattaccccg | gaaaccgatt | tgtttctgct | tggcttggac | 120 |
| tcggtaaccg | ccgttaatct | gatcgtcagt | ttggaaagcc | atttcgggat | cacgtttaac | 180 |
| gacgacgaac | tgatcgtgga | aaatttttcg | acggtgcgga | aaattacgga | acatgtgacg | 240 |
| gtcaaacttg | aggaagccct | atga | | | | 264 |

<210> SEQ ID NO 22
<211> LENGTH: 1259
<212> TYPE: DNA
<213> ORGANISM: Bacillus circulans

<400> SEQUENCE: 22

| | | | | | |
|---|---|---|---|---|---|
| atgaagttca | ctcatccgct | ggattattat | cgtctgaacg | gcaaacaaat | cctgtggtac | 60 |
| atgaatatcg | gcgaagatca | ggacagccag | gcgtcgaatt | actttccctc | cgtcaaggac | 120 |
| cctcaatccg | agaagattgt | cgtgcagcag | gagcaacagc | ttctcttttct | ggcgaggccg | 180 |
| caggacacgt | tatttttttca | tacgatgccg | gagcaagcct | tctcgatta | ttggaaagag | 240 |
| cgccgcctct | ccttgccgtc | gataatttgt | tgcgacaaac | tttcgcaagt | gcctgatctt | 300 |
| gagcgttata | cgattatccc | gtttattgtt | tcggatcaac | tgcttgagct | gaagcggcgg | 360 |
| tatccgcata | tggatatcat | tgcgccggat | ttggcggtct | gccgggaaat | caatcataag | 420 |
| ttcaatacga | aagacttat | ggagaggaac | gggtttaacg | tcacaacggg | ttatttctgc | 480 |
| agcgatatcg | agagcttgga | gcatgcctac | gaacagctca | tttccgccgg | cttttccaaa | 540 |
| tgcgtgttga | agttccata | cggctcgtcg | ggtaaaggtc | tcaaagtcat | cgacaacgaa | 600 |
| cggaatttcc | gttttttgct | gaattatatt | caaaaccgcc | agacaaacgt | cgacctgctc | 660 |
| ctggaaggct | ggcatcccca | ccgtctcagc | ctgacgtctc | agcttttcat | taccgaatat | 720 |
| gaagtccatc | ttctggccgt | caccgagcaa | atcatagacc | cgaacggtgt | ctataaagga | 780 |
| acgaattta | cgcctgcctt | atcgcaatcg | gaagcggccg | attatcgtga | agaaatctta | 840 |
| cgggcaggag | aactgatacg | gcagatgggg | tatagggggcg | tgcttgggat | cgattcgatc | 900 |
| ctcgatacga | acggagaact | gattccggtt | atcgagatta | cgccaggct | cactcaggtc | 960 |
| acctatattc | ttccgttggt | tatcgaacag | aaaaagcgtt | atgagtttgt | cgaaagcagg | 1020 |
| gtgctggtgt | ttaattccag | agcggatctg | gattttgaag | attacgaaaa | cgatctctcg | 1080 |
| gaagtgaccc | gcgatttacc | ggtccgaatc | gatctttaca | atttctgcaa | ggcttcggga | 1140 |
| gcctttaaaa | acacctataa | gctctttgtg | ttagtttctg | cccacaattc | gaacagctg | 1200 |
| ataaaagccc | gaagcctgct | tgacgagctg | aacacgaaaa | tgacaacggc | tgttcatta | 1259 |

<210> SEQ ID NO 23
<211> LENGTH: 1287
<212> TYPE: DNA
<213> ORGANISM: Bacillus circulans

<400> SEQUENCE: 23

| | | | | | |
|---|---|---|---|---|---|
| atgaacctgg | atcaagctga | aatcacggcc | ttaacgaaaa | ggtttgagac | tcctttttat | 60 |
| ttgtatgacg | gcgatttat | cgaagcgcat | taccggcaat | taagaagccg | gacgaacccg | 120 |

```
gcgatccagt tttatttgtc cctaaaagca aataacaata ttcatctggc caaattgttc      180
cggcagtggg gacttggcgt cgaggttgca tccgccggag aactcgcttt agcccggcat      240
gccggatttt cagccgaaaa catcattttc tcgggaccgg ggaagaagcg gagcgagctc      300
gagattgccg ttcaaagcgg gatttactgc atcatcgcgg aatccgttga agaactcttt      360
tacatagaag aactggctga aaagaaaac aaaacggccc gcgtcgcgat ccggatcaat       420
cccgataaaa gcttcggcag cacggccatc aaaatgggcg gagtaccgag acagttcgga      480
atggacgaat ccatgctgga tgccgtaatg gatgccgtcc gctctcttca attcaccaaa      540
tttatcggga tacacgtata taccggaacc cagaatctga ataccgacag cattatcgag      600
tcgatgaaat acaccgtaga tctaggcaga aacatttatg aacgatacgg aatcgtctgt      660
gaatgtatta atcttggcgg agggttcgga gtcccgtatt tttcacacga aaaggcactg      720
gatatcggca aaatcacgcg tacggtcagc gattacgttc aagaggcgag ggatacacgg      780
ttcccgcaaa cgacctttat tatcgaaagc ggaagatact tattggctca agcggccgtg      840
tatgtaaccg aggtgcttta ccggaaagcg tccaaggag  aagttttttgt gatcgtagac      900 gggggaatgc accaccatgc ggcctccact ttccggggaa gaagtatgcg gagcaactac      960
cccatggaat atattcccgt tagggaagac tccggccgtc gcgaactcga aaagtcacc      1020 attgccggtc ctctctgtac gcccgaagat tgtctaggga aggatgtcca tgtgccggcc     1080
ttgtatccgg gcgacctcgt atgtgtgttg aactcgggag cttacggact gagctttagc     1140
ccggttcatt ttctgggca cccgacgccc attgaaattc tcaaacgaa cggttcatac      1200 gagctgatca gacggaaagg aacggcggat gatatagtcg ccacccagct gcagacagaa     1260
tcaaatctcc tctttgtgga caaatag                                         1287

<210> SEQ ID NO 24
<211> LENGTH: 1026
<212> TYPE: DNA
<213> ORGANISM: Bacillus circulans

<400> SEQUENCE: 24
atgattgcat tggatacgat tcagtattat ggccaaattc caggcgtcaa ccattataac       60
ggcaagaaag aatttatgga aaacgccgtt aaaatcgcgc agctgtccga tgcttacggc      120
atagtcgggt ccctgtcgtt ttttaaccat tccgtattgg acccttgggc cgtaagctcg      180
gttattatgc ggcatacgga acgtcatgtt cctctaattg cgcttcagcc ctacatgtat      240 cctcccctata cggctgccaa gttaattcag agcttcactt atttgtacga ccggcggatc      300
gacttgaata tgatcaccgg ggccgttacc ggcgagctcc agcaaaccgg gggctatatc      360
gatcattcgt ccgctacaa gaaacttcac gaatatgttc aggtgctccg tctgctgctt      420
gaatccgatt ctgccgtttc gttcaaaggg gactattatg agctgaataa tttggagttc      480
aagcctttgc tgccggacaa acggcttttc ccgcgcatat ttatgtccgg ttcttccgag      540
gaagggcttg aaacgggttt gaaagcggcg gatttcgtcg ttactcatcc gggaccgctg      600
gaacatttta acgccatttt tagcgaaaag gtgcagggat cggctgttca aagtgccata      660
agaatcgaga ttatcgccag agaatcgcg gagcaagcat ggaagatcgc tcatgcccgt      720
tatcccggca accggcaggg gaagatccag ctccggatga aacaaattc ggaatcaagc      780 tggcagcgga tgctggccga actggcttta gcgagtgaaa cgtacgatga agtcttctgg      840
atgggcgggt acatgaacgg cggaatttac agtcccgtgt tagtcgggga ttacgagcaa      900
```

```
gtggccgctt atttgaatga gtattacaaa ctcggcgtga aagccgtgtt gctgggttcc        960
atgtacagcg aggaggattt tattcatttc agccgggtga aggaaggaat ttcgaatccg       1020
gtctag                                                                  1026

<210> SEQ ID NO 25
<211> LENGTH: 576
<212> TYPE: DNA
<213> ORGANISM: Bacillus circulans

<400> SEQUENCE: 25
gtggctcatc cgaatttgca gcagtcccgt gtcaacaaac gttgggtgga ggaattgaaa         60
aaacatcccg gcgaggttac cgtgcatgaa ctgtacggcg cgtatccgga gaaggtattg        120
gatatcgggc gggagcaggc tttgctggcg gaatgtgaac gtctcgtgct gcagtttccg        180
cttcaatggt acagcacacc gccgcttctg aagcagtggc tcgatgaagt gttcacaacg        240
gggtggctgt tcggtccggg cggtaaagcc gtagccggaa agaactcct gatcgccgtt         300 tctatcgggg gagcggcgga gacttacgag gcgggcggcc tgatcgggta cacgatcagt       360
gaattgaccc gccctctgca agctttcgcc aatcagatcg gcatgacgat gcttccgcac       420
tttaaatttc acggtgcgaa tcaggcggcg gacgaactga tcgagagcag cgcggagcga       480
tacgtcaggc atatcttgac tcccgagctt gatccccgga ttgcccggcg gagaatgctt       540
aatgacatga aacagaagat gcaggcctcc ctgtaa                                  576

<210> SEQ ID NO 26
<211> LENGTH: 1266
<212> TYPE: DNA
<213> ORGANISM: Streptomyces fradiae

<400> SEQUENCE: 26
gtgcgtgtgc tgcggctcac ccccttcttc caccacgact gcgtcaccgc ctggcccgcg         60
gagttcgacg ccgtcggggg catgcaggtg cagatcctcc gcctctcgcg ggaactggcc       120
gaccgcggcg tggagcagct cgtcatgacc gtcgggttcc ccggcctgcc cagggagcgc       180
gtcgaccggc ccggcctccg ggtccgggtc accggggcgc cgctgccccg gctgcgctcc       240
gaactgaccg gcctcgtggg gctcaaccag gcgtggctcg ccgcggtgct gacggcctgt       300
gcgccgctgc gccgcacctg gagggcccgac ctggtgcacg tccacgcgga cggccagctc       360
tgggcgctgc tcgccgggcc gctcgtctcg cgtctggtcg gcgcgccgta ctgcctcacc       420
ctgcactgct cgcggctggc ctcgtacgag ccgatgtccc gcttcgaccg gctccagcac       480
cggctggtgg cggcggccga gcggtacgcg ctgcggcggg cgcgccgggt gtcgacgctg       540
acctcgcgca ccgcggacac ggtggcgcgg ctgctgccgc tcgaccgggc cctggtggac       600
gtgctgcccg actcggtcgg cgacgtgcgg ccggtggcgc ggccggaggc cgaggagtac       660
gtgcggtcgc tcggcgtgcc cgccggggcg gcggtggtgg gctgggtcgg ccgggtcgcg       720
cacgagaagg ggtggcggga cttcgtcgcg atggcggagc ggtgggacgc cgggtcgggc       780
gccccggggg cggtgttcgc cgtggtgggc gacgggccgc agcgggagcg gatgcgggag       840
gcggtcgagg cggcggggct cgcggaccgg ttcgtgttca ccggtttcct gccccatgac       900
gccgtgccgt ccgtgatgac ggcgctggac gtcctcgtca tgccgtccgc ccacgaggag       960 ctggcggca gcgcgctgga ggccatggtg tgcggcacgc ccgtcgcggg ctacgcggtc      1020
ggcgggctgc gcgacacggt cggctcggtc acgccctccc tgctcgtccc gcggggcgac      1080
gtggcggcgc tgacccgcgc cgccggcgac gcggtcacgg acgccgaacg gcaccgcaag      1140
```

```
acggtcgcgg cggccgttcc cgacctgctg ggccggtacg gcgcggacac cgtcgagcgg    1200
gcgctggagc actaccggct ggccgtcggc cgggcgtccg gagggggtgc cgggtgggcg    1260
ccgtga                                                                1266
```

<210> SEQ ID NO 27
<211> LENGTH: 27
<212> TYPE: DNA
<213> ORGANISM: Artificial Sequence
<220> FEATURE:
<223> OTHER INFORMATION: forward primer for kanA-kanB

<400> SEQUENCE: 27
cccggatccg aatccccctt cgtgacg                                          27

<210> SEQ ID NO 28
<211> LENGTH: 30
<212> TYPE: DNA
<213> ORGANISM: Artificial Sequence
<220> FEATURE:
<223> OTHER INFORMATION: reverse primer for kanA-kanB

<400> SEQUENCE: 28
gtgactagtg ttcgtcgacc accgcgtcga                                       30

<210> SEQ ID NO 29
<211> LENGTH: 28
<212> TYPE: DNA
<213> ORGANISM: Artificial Sequence
<220> FEATURE:
<223> OTHER INFORMATION: forward primer for kanK

<400> SEQUENCE: 29
gcttctagaa ctccggagca cccgtgca                                         28

<210> SEQ ID NO 30
<211> LENGTH: 30
<212> TYPE: DNA
<213> ORGANISM: Artificial Sequence
<220> FEATURE:
<223> OTHER INFORMATION: reverse primer for kanK

<400> SEQUENCE: 30
gtgaagcttc gtggtgccgg acaggcccta                                       30

<210> SEQ ID NO 31
<211> LENGTH: 30
<212> TYPE: DNA
<213> ORGANISM: Artificial Sequence
<220> FEATURE:
<223> OTHER INFORMATION: forward primer for kanC

<400> SEQUENCE: 31
gggacctcta gaacgcggtg gtcgacgaac                                       30

<210> SEQ ID NO 32
<211> LENGTH: 36
<212> TYPE: DNA
<213> ORGANISM: Artificial Sequence
<220> FEATURE:
<223> OTHER INFORMATION: reverse primer for kanC

<400> SEQUENCE: 32
tcttccaagc ttactagttg tcggcggtcg ccccga                                36

<210> SEQ ID NO 33
<211> LENGTH: 30
<212> TYPE: DNA
<213> ORGANISM: Artificial Sequence
<220> FEATURE:
<223> OTHER INFORMATION: forward primer for kanD

<400> SEQUENCE: 33
gaccgctcta gacacctccg aggtcctctc                                    30

<210> SEQ ID NO 34
<211> LENGTH: 34
<212> TYPE: DNA
<213> ORGANISM: Artificial Sequence
<220> FEATURE:
<223> OTHER INFORMATION: reverse primer for kanD

<400> SEQUENCE: 34
tgaaaagctt actagtgggt gacgagacgc cggg                               34

<210> SEQ ID NO 35
<211> LENGTH: 33
<212> TYPE: DNA
<213> ORGANISM: Artificial Sequence
<220> FEATURE:
<223> OTHER INFORMATION: forward primer for kanE

<400> SEQUENCE: 35
acatctagag gctccggaag accgccgacg cca                                33

<210> SEQ ID NO 36
<211> LENGTH: 33
<212> TYPE: DNA
<213> ORGANISM: Artificial Sequence
<220> FEATURE:
<223> OTHER INFORMATION: reverse primer for kanE

<400> SEQUENCE: 36
tcgaagctta ctagtgagac gaggaggacc ctt                                33

<210> SEQ ID NO 37
<211> LENGTH: 30
<212> TYPE: DNA
<213> ORGANISM: Artificial Sequence
<220> FEATURE:
<223> OTHER INFORMATION: forward primer for kanF

<400> SEQUENCE: 37
cgaggctcta gagccggacc agaacccatt                                    30

<210> SEQ ID NO 38
<211> LENGTH: 36
<212> TYPE: DNA
<213> ORGANISM: Artificial Sequence
<220> FEATURE:
<223> OTHER INFORMATION: reverse primer for kanF

<400> SEQUENCE: 38
tagaacaagc ttactagtac gtcgggtgtc gtacgg                             36

<210> SEQ ID NO 39
<211> LENGTH: 30
<212> TYPE: DNA
<213> ORGANISM: Artificial Sequence
<220> FEATURE:
<223> OTHER INFORMATION: forward primer for kanI-kacL

```
<400> SEQUENCE: 39
gatcgctcta gacacctggt tctggttccc                                        30

<210> SEQ ID NO 40
<211> LENGTH: 36
<212> TYPE: DNA
<213> ORGANISM: Artificial Sequence
<220> FEATURE:
<223> OTHER INFORMATION: reverse primer for kanI-kacL

<400> SEQUENCE: 40
aggggaaagc ttactagtgt caggagatgc cgaccg                                 36

<210> SEQ ID NO 41
<211> LENGTH: 30
<212> TYPE: DNA
<213> ORGANISM: Artificial Sequence
<220> FEATURE:
<223> OTHER INFORMATION: forward primer for kacA

<400> SEQUENCE: 41
ggcgtctaga taccgggaga tcgggctgtg                                        30

<210> SEQ ID NO 42
<211> LENGTH: 35
<212> TYPE: DNA
<213> ORGANISM: Artificial Sequence
<220> FEATURE:
<223> OTHER INFORMATION: reverse primer for kacA

<400> SEQUENCE: 42
acaaagctta ctagttgctc atagcgactc cttgt                                  35

<210> SEQ ID NO 43
<211> LENGTH: 29
<212> TYPE: DNA
<213> ORGANISM: Artificial Sequence
<220> FEATURE:
<223> OTHER INFORMATION: forward primer for nemD

<400> SEQUENCE: 43
cactctagac atcgccgtcc tctccccgt                                         29

<210> SEQ ID NO 44
<211> LENGTH: 33
<212> TYPE: DNA
<213> ORGANISM: Artificial Sequence
<220> FEATURE:
<223> OTHER INFORMATION: reverse primer for nemD

<400> SEQUENCE: 44
tcaaagctta ctagtggcgc agatacggcg cac                                    33

<210> SEQ ID NO 45
<211> LENGTH: 27
<212> TYPE: DNA
<213> ORGANISM: Artificial Sequence
<220> FEATURE:
<223> OTHER INFORMATION: forward primer for tobM1

<400> SEQUENCE: 45
ccgtctagac cgcccttttcc ccgcaac                                          27

<210> SEQ ID NO 46
```

```
<211> LENGTH: 33
<212> TYPE: DNA
<213> ORGANISM: Artificial Sequence
<220> FEATURE:
<223> OTHER INFORMATION: reverse primer for tobM1

<400> SEQUENCE: 46
gataagctta ctagtcacac cgtcctattc ctg                              33

<210> SEQ ID NO 47
<211> LENGTH: 26
<212> TYPE: DNA
<213> ORGANISM: Artificial Sequence
<220> FEATURE:
<223> OTHER INFORMATION: forward primer for tobM2

<400> SEQUENCE: 47
cgatctagac cgggaggcga ccgtgt                                      26

<210> SEQ ID NO 48
<211> LENGTH: 33
<212> TYPE: DNA
<213> ORGANISM: Artificial Sequence
<220> FEATURE:
<223> OTHER INFORMATION: reverse primer for tobM2

<400> SEQUENCE: 48
gcgaagctta ctagttcaga cgcatacgcc cag                              33

<210> SEQ ID NO 49
<211> LENGTH: 31
<212> TYPE: DNA
<213> ORGANISM: Artificial Sequence
<220> FEATURE:
<223> OTHER INFORMATION: forward primer for gtmG

<400> SEQUENCE: 49
tgtcctctag agctgcccgg tcacttcccg c                                31

<210> SEQ ID NO 50
<211> LENGTH: 33
<212> TYPE: DNA
<213> ORGANISM: Artificial Sequence
<220> FEATURE:
<223> OTHER INFORMATION: reverse primer for gtmG

<400> SEQUENCE: 50
aaaaagctta ctagtcactc ttccggaaga atc                              33

<210> SEQ ID NO 51
<211> LENGTH: 27
<212> TYPE: DNA
<213> ORGANISM: Artificial Sequence
<220> FEATURE:
<223> OTHER INFORMATION: forward primer for btrG-btrH

<400> SEQUENCE: 51
ttctctagat ctaggaaacc gcatgcc                                     27

<210> SEQ ID NO 52
<211> LENGTH: 35
<212> TYPE: DNA
<213> ORGANISM: Artificial Sequence
<220> FEATURE:
<223> OTHER INFORMATION: reverse primer for btrG-btrH

<400> SEQUENCE: 52
```
ggctacgtaa aactagtggt ttatccgctt ttgct                     35

<210> SEQ ID NO 53
<211> LENGTH: 27
<212> TYPE: DNA
<213> ORGANISM: Artificial Sequence
<220> FEATURE:
<223> OTHER INFORMATION: forward primer for btrI-btrJ

<400> SEQUENCE: 53
acctctagac ggaaaccgcc atcccat                              27

<210> SEQ ID NO 54
<211> LENGTH: 35
<212> TYPE: DNA
<213> ORGANISM: Artificial Sequence
<220> FEATURE:
<223> OTHER INFORMATION: reverse primer for btrI-btrJ

<400> SEQUENCE: 54
tcctacgtaa aactagtgag ttaatgaaca gccgt                     35

<210> SEQ ID NO 55
<211> LENGTH: 27
<212> TYPE: DNA
<213> ORGANISM: Artificial Sequence
<220> FEATURE:
<223> OTHER INFORMATION: forward primer for btrK-btrO

<400> SEQUENCE: 55
agctctagaa agcccgaagc ctgcttg                              27

<210> SEQ ID NO 56
<211> LENGTH: 35
<212> TYPE: DNA
<213> ORGANISM: Artificial Sequence
<220> FEATURE:
<223> OTHER INFORMATION: reverse primer for btrK-btrO

<400> SEQUENCE: 56
gtttacgtaa aactagttcc ctagaccgga ttcga                     35

<210> SEQ ID NO 57
<211> LENGTH: 27
<212> TYPE: DNA
<213> ORGANISM: Artificial Sequence
<220> FEATURE:
<223> OTHER INFORMATION: forward primer for btrV

<400> SEQUENCE: 57
tattctagaa ttgacttata actcaat                              27

<210> SEQ ID NO 58
<211> LENGTH: 35
<212> TYPE: DNA
<213> ORGANISM: Artificial Sequence
<220> FEATURE:
<223> OTHER INFORMATION: reverse primer for btrV

<400> SEQUENCE: 58
cattacgtaa aactagtatc cgaacgtcac ataag                     35

<210> SEQ ID NO 59
<211> LENGTH: 27
<212> TYPE: DNA

```
<213> ORGANISM: Artificial Sequence
<220> FEATURE:
<223> OTHER INFORMATION: forward primer for aprD3

<400> SEQUENCE: 59
ggttctagat gatggacgtg gccgcga                                          27

<210> SEQ ID NO 60
<211> LENGTH: 33
<212> TYPE: DNA
<213> ORGANISM: Artificial Sequence
<220> FEATURE:
<223> OTHER INFORMATION: reverse primer for aprD3

<400> SEQUENCE: 60
cttaagctta ctagtgggcc gtcggtcgtc ctg                                   33

<210> SEQ ID NO 61
<211> LENGTH: 30
<212> TYPE: DNA
<213> ORGANISM: Artificial Sequence
<220> FEATURE:
<223> OTHER INFORMATION: forward primer for aprD4

<400> SEQUENCE: 61
ggctctagaa accccaccct caccatccag                                       30

<210> SEQ ID NO 62
<211> LENGTH: 33
<212> TYPE: DNA
<213> ORGANISM: Artificial Sequence
<220> FEATURE:
<223> OTHER INFORMATION: reverse primer for aprD4

<400> SEQUENCE: 62
cgcaagctta ctagtatcgt gtggtctccg gct                                   33
```